(12) United States Patent
Dust et al.

(10) Patent No.: US 11,335,446 B2
(45) Date of Patent: *May 17, 2022

(54) METHOD OF OPTIMIZING HEALTHCARE SERVICES CONSUMPTION

(71) Applicant: Quality Healthcare Intermediary, LLC, Indianapolis, IN (US)

(72) Inventors: Larry R. Dust, Indianapolis, IN (US); David B. Cook, Indianapolis, IN (US)

(73) Assignee: Quality Healthcare Intermediary, LLC, Indianapolis, IN (US)

( * ) Notice: Subject to any disclaimer, the term of this patent is extended or adjusted under 35 U.S.C. 154(b) by 221 days.

This patent is subject to a terminal disclaimer.

(21) Appl. No.: 16/847,037

(22) Filed: Apr. 13, 2020

(65) Prior Publication Data

US 2020/0243189 A1 Jul. 30, 2020

Related U.S. Application Data

(63) Continuation of application No. 16/405,408, filed on May 7, 2019, now Pat. No. 10,622,106, which is a
(Continued)

(51) Int. Cl.
*G16H 20/10* (2018.01)
*G06Q 30/02* (2012.01)
(Continued)

(52) U.S. Cl.
CPC ............ *G16H 20/10* (2018.01); *G06Q 10/00* (2013.01); *G06Q 30/0201* (2013.01);
(Continued)

(58) Field of Classification Search
CPC ........ G06Q 50/22; G06Q 50/24; G06Q 40/08; G06Q 30/0201; G06F 19/00; G06F 19/30;
(Continued)

(56) References Cited

U.S. PATENT DOCUMENTS

| 4,831,526 A | 5/1989 | Luchs et al. |
| 4,916,611 A | 4/1990 | Doyle et al. |

(Continued)

FOREIGN PATENT DOCUMENTS

| CN | 104376875 A | 2/2015 |
| EP | 0917078 A1 | 5/1999 |
| JP | 2001-331649 A | 11/2001 |

OTHER PUBLICATIONS

"Periodically" as defined by Free Meriam-Webster Dictionary, www.meriam-webster.com/dictionary/periodically, dated Jan. 28, 2014; 1 page (Coresource Exhibit 1004).
(Continued)

*Primary Examiner* — Jason S Tiedeman
(74) *Attorney, Agent, or Firm* — Faegre Drinker Biddle & Reath

(57) ABSTRACT

A method of optimizing healthcare services consumption according to the invention includes the steps of assessing the healthcare situation of an employer providing healthcare benefits to a population, identifying a first group of patients from the population likely to generate expensive healthcare claims based on data representing past claims, periodically determining whether patients in the first group have satisfied certain predetermined healthcare requirements, identifying a first group of providers who provide high quality, cost efficient healthcare services based on the practice patterns of the providers, prompting patients who have not satisfied the predetermined healthcare requirements to obtain services from providers in the first group, and responding to healthcare requests from patients by determining whether the requesting patient is seeking services from a provider in the first group, and, if not, urging the patient to obtain such services from a provider in the first group.

27 Claims, 17 Drawing Sheets

Chronic Condition Report

| Chronic Condition | Number of Conditions Based on Active Membership | Number of Conditions with at Least 12 Months of Claims History | Number of Conditions Meeting Minimum Annual Care Requirements | Minimum Care Rate | Minimum Annual Care Recommended | Estimated Annual Cost of Minimum Services Per Person |
|---|---|---|---|---|---|---|
| Hyperlipidemia | 561 | 467 | 160 | 33% | 1 Blood Lipid<br>1 Clinical Evaluation | $70 |
| Asthma | 192 | 163 | 46 | 26% | 2 Clinical Evaluations | $103 |
| Diabetes | 180 | 150 | 1 | 1% | 2 Clinical Evaluations<br>2 Glycohemoglobins<br>1 Microalbumin<br>1 Retinal Exam<br>1 Serum Lipids | $290 |
| Coronary Artery Disease | 130 | 73 | 12 | 16% | 1 Clinical Evaluation<br>1 EKG<br>1 Serum Lipids | $139 |
| Chronic Obstructive Pulmonary Disease | 99 | 86 | 42 | 49% | 2 Clinical Evaluations | $103 |
| Hypothyroidism | 95 | 84 | 37 | 44% | 1 Clinical Evaluation<br>1 TSH or T4 | $93 |

Related U.S. Application Data continuation of application No. 15/584,664, filed on May 2, 2017, now Pat. No. 10,325,069, which is a continuation of application No. 14/278,750, filed on May 15, 2014, now abandoned, and a continuation of application No. 13/742,625, filed on Jan. 16, 2013, now abandoned, which is a continuation of application No. 13/178,174, filed on Jul. 7, 2011, now Pat. No. 8,489,420, which is a continuation of application No. 12/773,334, filed on May 4, 2010, now Pat. No. 8,036,916, which is a continuation of application No. 10/313,370, filed on Dec. 6, 2002, now Pat. No. 7,711,577.

(51) Int. Cl.
*G06Q 40/08* (2012.01)
*G16H 50/30* (2018.01)
*G16H 20/00* (2018.01)
*G06Q 10/00* (2012.01)
*G16H 40/20* (2018.01)
*G06F 11/00* (2006.01)
*G06F 11/07* (2006.01)

(52) U.S. Cl.
CPC .............. *G06Q 40/08* (2013.01); *G16H 20/00* (2018.01); *G16H 40/20* (2018.01); *G16H 50/30* (2018.01); *G06F 11/008* (2013.01); *G06F 11/0727* (2013.01); *G06F 11/0751* (2013.01)

(58) Field of Classification Search
CPC ...... G06F 19/32; G06F 19/325; G06F 19/328; G06F 19/34; G06F 19/3418; G06F 19/36; G16H 10/00; G16H 10/60; G16H 15/00; G16H 20/00; G16H 50/00; G16H 50/30; G16H 50/70; G16H 80/00
USPC ........................................................ 705/2, 3
See application file for complete search history.

(56) References Cited

U.S. PATENT DOCUMENTS

| | | | |
|---|---|---|---|
| 4,975,840 A | 12/1990 | Detore et al. | |
| 5,301,105 A | 4/1994 | Cummings, Jr. | |
| 5,365,425 A | 11/1994 | Torma et al. | |
| 5,486,999 A | 1/1996 | Mebane | |
| 5,508,912 A | 4/1996 | Schneiderman | |
| 5,557,514 A | 9/1996 | Seare et al. | |
| 5,583,758 A | 12/1996 | McIlroy et al. | |
| 5,590,037 A | 12/1996 | Ryan et al. | |
| 5,652,842 A | 7/1997 | Siegrist et al. | |
| 5,655,085 A | 8/1997 | Ryan et al. | |
| 5,706,441 A | 1/1998 | Lockwood | |
| 5,724,379 A | 3/1998 | Perkins et al. | |
| 5,764,923 A | 6/1998 | Tallman et al. | |
| 5,778,345 A | 7/1998 | McCartney | |
| 5,819,228 A | 10/1998 | Spiro | |
| 5,835,897 A | 11/1998 | Dang | |
| 5,839,113 A | 11/1998 | Federau et al. | |
| 5,839,118 A | 11/1998 | Ryan et al. | |
| 5,908,383 A | 6/1999 | Brynjestad | |
| 5,924,073 A | 7/1999 | Tyuluman et al. | |
| 5,953,704 A | 9/1999 | McIlroy et al. | |
| 5,956,689 A | 9/1999 | Everhart, III | |
| 5,956,691 A | 9/1999 | Powers | |
| 5,964,700 A | 10/1999 | Tallman et al. | |
| 6,009,402 A | 12/1999 | Whitworth | |
| 6,014,629 A | 1/2000 | Debruin-Ashton | |
| 6,014,632 A | 1/2000 | Gamble et al. | |
| 6,032,119 A | 2/2000 | Brown et al. | |
| 6,078,890 A | 6/2000 | Mangin et al. | |
| 6,151,581 A | 11/2000 | Kraftson et al. | |
| 6,151,586 A | 11/2000 | Brown | |
| 6,223,164 B1 | 4/2001 | Seare et al. | |
| 6,269,339 B1 | 7/2001 | Silver | |
| 6,381,576 B1 | 4/2002 | Gilbert | |
| 6,385,589 B1 | 5/2002 | Trusheim et al. | |
| 6,615,181 B1 | 9/2003 | Segal | |
| 6,684,190 B1 | 1/2004 | Powers et al. | |
| 6,735,569 B1 | 5/2004 | Wizig | |
| 6,986,075 B2 | 1/2006 | Ackaret et al. | |
| 7,127,407 B1 | 10/2006 | Averill et al. | |
| 7,287,031 B1 | 10/2007 | Karpf et al. | |
| 7,337,123 B2 | 2/2008 | Dvorak et al. | |
| 7,624,028 B1 * | 11/2009 | Brown | A61B 5/150854 705/3 |
| 7,640,175 B1 | 12/2009 | Prasad et al. | |
| 7,698,155 B1 * | 4/2010 | Prasad | G16H 70/40 705/3 |
| 7,711,577 B2 | 5/2010 | Dust et al. | |
| 7,739,124 B1 | 6/2010 | Walker et al. | |
| 7,797,172 B2 * | 9/2010 | Fitzgerald | G06Q 40/02 705/4 |
| 7,953,615 B2 | 5/2011 | Aquila et al. | |
| 8,036,916 B2 | 10/2011 | Dust et al. | |
| 8,316,263 B1 | 11/2012 | Gough et al. | |
| 8,489,420 B2 | 7/2013 | Dust et al. | |
| 8,707,105 B2 | 4/2014 | Grube et al. | |
| 9,141,457 B1 | 9/2015 | Ma et al. | |
| 9,678,817 B1 | 6/2017 | Hasbun et al. | |
| 10,157,090 B2 | 12/2018 | Hasbun et al. | |
| 10,325,069 B2 | 6/2019 | Dust et al. | |
| 10,622,106 B2 | 4/2020 | Dust et al. | |
| 2001/0020229 A1 | 9/2001 | Lash | |
| 2001/0023404 A1 | 9/2001 | Ogawa et al. | |
| 2001/0037214 A1 | 11/2001 | Raskin et al. | |
| 2001/0039503 A1 | 11/2001 | Chan et al. | |
| 2001/0044735 A1 | 11/2001 | Colburn et al. | |
| 2002/0004725 A1 | 1/2002 | Martin et al. | |
| 2002/0004757 A1 | 1/2002 | Torres et al. | |
| 2002/0010598 A1 | 1/2002 | Johnson et al. | |
| 2002/0019748 A1 | 2/2002 | Brown | |
| 2002/0019786 A1 | 2/2002 | Gonzalez et al. | |
| 2002/0026334 A1 | 2/2002 | Igoe | |
| 2002/0049617 A1 | 4/2002 | Lencki et al. | |
| 2002/0072933 A1 | 6/2002 | Vonk et al. | |
| 2002/0077849 A1 | 6/2002 | Baruch et al. | |
| 2002/0082480 A1 * | 6/2002 | Riff | G16H 40/67 600/300 |
| 2002/0087355 A1 | 7/2002 | Rowlandson | |
| 2002/0103680 A1 | 8/2002 | Newman | |
| 2002/0111826 A1 | 8/2002 | Potter et al. | |
| 2002/0116221 A1 | 8/2002 | Fields et al. | |
| 2002/0120187 A1 | 8/2002 | Eiffert et al. | |
| 2002/0133386 A1 | 9/2002 | Chishti et al. | |
| 2002/0143680 A1 | 10/2002 | Walters et al. | |
| 2002/0169635 A1 | 11/2002 | Shillingburg | |
| 2002/0173992 A1 | 11/2002 | Dang | |
| 2002/0188484 A1 | 12/2002 | Grover et al. | |
| 2002/0194033 A1 | 12/2002 | Huff | |
| 2003/0011646 A1 | 1/2003 | Levine et al. | |
| 2003/0018240 A1 | 1/2003 | Goetzke et al. | |
| 2003/0046113 A1 | 3/2003 | Johnson et al. | |
| 2003/0060688 A1 | 3/2003 | Ciarniello et al. | |
| 2003/0097185 A1 | 5/2003 | Goetzke et al. | |
| 2003/0101075 A1 | 5/2003 | Ban et al. | |
| 2003/0126101 A1 * | 7/2003 | Rao | G16H 70/60 706/12 |
| 2003/0163349 A1 | 8/2003 | Ho | |
| 2003/0167189 A1 | 9/2003 | Lutgen et al. | |
| 2003/0195771 A1 | 10/2003 | Fitzgerald et al. | |
| 2003/0216937 A1 | 11/2003 | Schreiber et al. | |
| 2003/0216946 A1 | 11/2003 | Ferraro | |
| 2004/0006488 A1 | 1/2004 | Fitall et al. | |
| 2004/0064341 A1 | 4/2004 | Langan et al. | |
| 2004/0083125 A1 | 4/2004 | Almeida et al. | |
| 2004/0103001 A1 | 5/2004 | Mazar et al. | |
| 2004/0111291 A1 | 6/2004 | Dust et al. | |
| 2004/0143446 A1 | 7/2004 | Lawrence | |
| 2006/0235280 A1 | 10/2006 | Vonk et al. | |

(56) References Cited

U.S. PATENT DOCUMENTS

| | | | |
|---|---|---|---|
| 2014/0200907 | A1 | 7/2014 | Dust et al. |
| 2014/0249842 | A1 | 9/2014 | Dust et al. |
| 2014/0249843 | A1 | 9/2014 | Dust et al. |
| 2015/0046635 | A1 | 2/2015 | Fitzpatrick et al. |
| 2015/0074467 | A1 | 3/2015 | Jacoby |
| 2015/0205657 | A1 | 7/2015 | Clark |
| 2019/0266042 | A1 | 8/2019 | Dust et al. |

OTHER PUBLICATIONS

A New Approach to Health Risk Assessment, IHCIS and Symmetry Health Data Systems, Feb. 2001.
Barsky, The Patient with Hypochondriasis, Nov. 8, 2011, New England Journal of Medicine 345:1395, Clinical Practice.
Bodenheimer, Physicians and the Changing Medical Marketplace, Feb. 18, 1999, N Engl J Med 340:584, Health Policy Report.
Copper et al., Comparing Health Care Systems, Godd Medicine, Fall 1994, 9 pages.
Decision, Institute of Covered Business Method Patent Review, PTAB, *Coresource, Inc. Petitioner v. Quality healthcare Intermediary, LLC*, Case CMB 2014-0062, U.S. Pat. No. 8,036,916, Entered Jul. 28, 2014; 25 pages.
Decision, Institute of Covered Business Method Patent Review, PTAB, *Coresource, Inc. Petitioner v. Quality healthcare Intermediary, LLC*, Case CMB 2014-0063, U.S. Pat. No. 8,489,420 B2, Entered Jul. 28, 2014; 22 pages.
Declaration of Richard Manning, PH.D, filed with PTAB, U.S. Pat. No. 8,036,916; 15 pages (Coresource Exhibit 1007).
Declaration of Richard Manning, PH.D, filed with PTAB, U.S. Pat. No. 8,489,420; 14 pages (Coresource Exhibit 1004).
Dranove, Determinants of managed care penetration, 1998, Journal of Health Economics, 17, 729-745.
Dudley, Manged care in transition, Apr. 5, 2001, The New England Journal of Medicine, vol. 344, No. 14, p. 1087-1092.
Duits, MTBF: Hard drive failure prediction?, May 19, 2015, Data Recovery Blog by Kroll Ontrak.
Gold, A National Survey of the Arrangements Managed-Care Plans Make With Physicians, Dec. 21, 1995, The New England Journal of Medicine, vol. 333 No. 25, p. 1678-1683.
Han, Historical Changes in the Objectives of the Periodic Health Examination, Nov. 15, 1997, Annals of Internal Medicine, vol. 127 Issue 10, pp. 910-917.
Holthof, Changing health-care systems, 1995, International Journal of Antimicrobial Agents, 5, 67-71.
Imielinski, Querying in Highly Mobile Distributed Environments, 1992, Proceedings of the 18th Conference on Very Large Databases, Morgan Kaufman pubs. (Los Altos CA), Vancouver.
Integrated Healthcare Information Services, Inc. "IHCIS" web pages, captured from ihcis.com by the Internet Archive: Wayback Machine in 2001, available at http://arcive.org—Coresource Exhibit 1014; 14 pages.
MEDecision Introduces CaseAlert (TM): Software Will Help Managed Care Organizations Identify High-Risk Patients; printed from Internet (http://www.prnewswire.com/news-releases/medecision-introduces-casealerttm-software-will-help-managed-care-organizations-identifyhigh-risk-patients-82310257.html); Oct. 13, 2014; 3 pages.
Ng, How far to the nearest physician?, Jul. 15, 1997, Canadian Medical Association Journal, vol. 8, No. 4, p. 19-31.
Perry, Physical access to primary health care in Andean Bolivia, May 2000, Social Science & Medicine, vol. 50, Issue 9, p. 1177-1188.
Petition for Covered Business Method filed with the PTAB on Jul. 7, 2011—U.S. Pat. No. 8,489,420; 85 pages.
Petition for Covered Business Method filed with the PTAB on May 4, 2010—U.S. Pat. No. 8,036,916; 89 pages.
Phibbs, A variable-radius measure of local hospital market structure, Health Serv Res. Aug. 1993; 28(3): 313-324.
Pinheiro, Weber, and Barroso, Failure Trends in a Large Disk Drive Population, Feb. 2007, Mountain View, CA; URL: http://thedatarecoveryblog.com/2015/05/19/mtbf-hard-drive-failure-predict-ion/.
Power of Attorney appointing Mark Nikolsky filed with PTAB, U.S. Pat. No. 8,489,420; 2 pages (Coresource Exhibit 1003).
*Quality Healthcare Intermediary, LLC v. Coresource, Inc.* Complaint filed on Jul. 19, 2013 in the U.S. District Court, Northern District of Illinois, Eastern Division, Case No. 13-CV-5182; 9 pages (Coresource Exhibit 1002).
Schelhammer, Steve, "The Accordant Story", Accordant Health Services web pages, captured from www.accordant.net by the Internet Archive: Wayback Machine in 2001, available at http://www.archive.org; Coresource Exhibit 1009; Oct. 22, 2013; 8 pages.
Sommers, A descriptive study of managed-care hassles in 26 practices, Mar. 2001, West J Med, 174, 175-179.
Stone, Cost-Utility Analyses of Clinical Preventive Services, 2000, Am J Prev Med, 19(1).
Taheri, Paying a Premium: How Patient Complexity Affects Costs and Profit Margins, 1999, Annals of Surgery, vol. 229, No. 6, 807-814.
Vistnes, Hospitals, Mergers, and Two-Stage Competition, 2000, Antitrust Law Journal 67, No. 3, 671-692.
Wiltshire, Mean Time Between Failures: Can It Help Predict Hard Drive Failure?, May 19, 2015, Data Blog by Kroll Ontrack, URL: http://blog.krollontrack.co.uk/concepts-explained/mean-time-between-failu-res-canit-help-predict-hard-drive-failure/.

\* cited by examiner

HEZ Service Coast Analysis

| Specialty, Network, or Hospital | Total Allowed Charges | Total Allowed Charges at Normative Costs | % Excess Charge | Excess Charge per Life per year |
|---|---|---|---|---|
| Cardiology | $4,251,526 | $4,488,559 | -5.3% | -$12.08 |
| Chemical Dependency | $170,457 | $158,575 | 7.5% | $0.61 |
| Dermatology | $1,202,770 | $1,114,273 | 7.9% | $4.51 |
| Endocrinology | $1,903,570 | $1,431,646 | 33.0% | $24.06 |
| Gastroenterology | $2,797,816 | $2,813,871 | -0.6% | -$0.82 |
| Gynecology | $2,907,812 | $2,888,889 | 0.7% | $0.96 |
| Hemtaology | $856,811 | $848,672 | 1.0% | $0.41 |
| Hepatology | $1,813,309 | $1,643,433 | 10.3% | $8.66 |
| Infectious Disease | $217,356 | $255,881 | -15.1% | -$1.96 |
| ○ | ○ | ○ | ○ | ○ |
| ○ | ○ | ○ | ○ | ○ |
| ○ | ○ | ○ | ○ | ○ |
| ○ | ○ | ○ | ○ | ○ |
| ○ | ○ | ○ | ○ | ○ |
| Grand Total all MPC's | $35,831,526 | $35,265,070 | 1.6% | $28.88 |
| PPO Network A | $20,289,527 | $19,827,685 | 2.3% | $23.54 |
| PPO Network B | $12,753,951 | $12,894,746 | -1.1% | -$7.18 |
| Hospital A | $9,758,638 | $9,756,274 | 0.0% | $0.12 |
| Hospital B | $5,573,549 | $5,726,413 | -2.7% | -$7.79 |

FIG. 5

| Specialty | Total Costs of Employer 10 | Normalized Costs of HEZ 24 | % Excess | Excess per Life per Year |
|---|---|---|---|---|
| Cardiology | $55,000 | $72,100 | -23.7% | -$43.45 |
| Chemical Dependency | $4,500 | $4,300 | +4.7% | +$0.71 |
| Dermatology | $38,400 | $12,900 | +29.8% | +$38.14 |
| ⊛ | ⊛ | ⊛ | ⊛ | ⊛ |
| ⊛ | ⊛ | ⊛ | ⊛ | ⊛ |
| ⊛ | ⊛ | ⊛ | ⊛ | ⊛ |
| ⊛ | ⊛ | ⊛ | ⊛ | ⊛ |
| ⊛ | ⊛ | ⊛ | ⊛ | ⊛ |
| ⊛ | ⊛ | ⊛ | ⊛ | ⊛ |
| 70 | 72 | 74 | 76 | 78 |

HEALTHCARE INDEX ANALYSIS

| | In this HEZ | Normative Value | % Excess | Cost per Life per Year |
|---|---|---|---|---|
| Number of Individuals in Analysis | 9,808 | | | |
| Average age of Adults (employees & spouses) | 42.0 | 41.9 | 0.24% | |
| % of Females in Adult Covered Population | 38.6% | 34.3% | 12.54% | |
| % of Adults in Covered Population | 74.8% | 65.9% | 13.51% | |
| Healthcare Index of Population | 1.506 | 1.00 | 50.6% | |
| Excess Cost Expected Due to Atypical Healthcare Index | $10,447,381 | | 32.3% | $532.59 |
| Excess of Healthcare Index due to Atypical Demographics | 0.108 | | 10.8% | |
| Excess Cost Expected Due to Atypical Demographics | $2,222,993 | | 6.5% | $113.33 |
| Excess of Healthcare Index due to Atypical Illness Burden | 0.398 | | 39.8% | |
| Excess Cost Expected Due to Atypical Illness Burden | $8,224,388 | | 25.8% | $419.27 |

FIG. 7

Chronic Condition Report ~94

| Chronic Condition | Number of Conditions Based on Active Membership | Number of Conditions with at Least 12 Months of Claims History | Number of Conditions Meeting Minimum Annual Care Requirements | Minimum Care Rate | Minimum Annual Care Recommended | Estimated Annual Cost of Minimum Services Per Person |
|---|---|---|---|---|---|---|
| Hyperlipidemia | 561 | 487 | 160 | 33% | 1 Blood Lipid<br>1 Clinical Evaluation | $70 |
| Asthma | 192 | 163 | 46 | 28% | 2 Clinical Evaluations | $103 |
| Diabetes | 180 | 150 | 1 | 1% | 2 Clinical Evaluations<br>2 Glycohemoglobins<br>1 Microalbumin<br>1 Retinal Exam<br>1 Serum Lipids | $290 |
| Coronary Artery Disease | 130 | 73 | 12 | 16% | 1 Clinical Evaluation<br>1 EKG<br>1 Serum Lipids | $139 |
| Chronic Obstructive Pulmonary Disease | 99 | 86 | 42 | 49% | 2 Clinical Evaluations | $103 |
| Hypothyroidism | 95 | 84 | 37 | 44% | 1 Clinical Evaluation<br>1 TSH or T4 | $93 |

Co-Morbidity Report

| Summary of Individuals with Chronic Conditions | Current | Percent of Total medical Lives - Current | Previous | Percent of Total Medical Lives - Previous | Percent of Total Medical Lives |
|---|---|---|---|---|---|
| Number of Individuals with 1 chronic condition | 619 | 17.1% | 608 | 17.0% | 7.1% |
| Number of Individuals with 2 chronic conditions | 236 | 6.5% | 205 | 5.7% | 2.5% |
| Number of Individuals with 3 chronic conditions | 86 | 2.4% | 77 | 2.1% | 0.8% |
| Number of Individuals with 4 chronic conditions | 34 | 0.9% | 23 | 0.6% | 0.2% |
| Number of Individuals with 5 chronic conditions | 12 | 0.3% | 8 | 0.2% | 0.1% |
| Number of Individuals with 6 chronic conditions | 4 | 0.1% | 5 | 0.1% | 0.0% |
| Number of Individuals with 7 chronic conditions | 0 | 0.0% | 1 | 0.0% | 0.0% |
| Number of Individuals with 8 chronic conditions | 0 | 0.0% | 1 | 0.0% | 0.0% |
| Number of Individuals with 9 chronic conditions | 2 | 0.1% | 0 | 0.0% | 0.0% |
| Total Number of Individuals with chronic conditions | 993 | | 928 | | |
| Total Number of Individuals with Medical Coverage | 3,618 | 27.4% | 3,586 | 25.7% | 11.9% |
| Chronic Condition Patient Rate | | | | | |
| Chronic Condition Patient Rate (Age Sex Adjusted) | | | | | 14.8% |
| Estimated annual cost of minimum care services based on employer experience | | | | | |

FIG. 9

Individual Healthcare Indices

| Family ID | Patient ID | Age | Gender | Healthcare Index | Predicted Cost |
|---|---|---|---|---|---|
| 9139k0178196 | s | 71 | M | 35.100 | $73,882 |
| 9139k0175223 | e | 52 | F | 28.649 | $60,304 |
| 294k0132278 | e | 51 | F | 25.192 | $53,028 |
| 9139k0174449 | s | 69 | M | 24.630 | $51,844 |
| 9139k0176852 | s | 58 | M | 24.370 | $51,296 |
| 9139k0175471 | e | 74 | F | 20.863 | $43,915 |
| 9139k0171637 | s | 34 | M | 20.467 | $43,082 |
| 9139k0177610 | s | 43 | M | 20.195 | $42,508 |
| 9139k0177861 | e | 59 | F | 20.060 | $42,224 |

NCQSP Listing

| PROVIDER ID | Name | CITY | STATE | ZIP | # of Episodes | Cost efficiency index |
|---|---|---|---|---|---|---|
| 224352 | Confidential | JACKSON | MS | 39225 | 157 | 4.18 |
| 108727 | Confidential | HENDERSONVILLE | NC | 28739 | 389 | 3.94 |
| 215019 | Confidential | OWNESBORO | KY | 42323 | 153 | 3.16 |
| 216053 | Confidential | YORKVILLE | IL | 60560 | 251 | 3.04 |
| 51319 | Confidential | LOS ANGELES | CA | 90045 | 186 | 2.98 |
| 256290 | Confidential | MOLINE | IL | 61266 | 357 | 2.70 |
| 240281 | Confidential | GRAND RAPIDS | MI | 49501 | 352 | 2.54 |
| 230027 | Confidential | MERIDIAN | MS | 39301 | 378 | 2.32 |
| 165611 | Confidential | CINCINNATI | OH | 45233 | 210 | 2.29 |

Fig. 15

METHOD OF OPTIMIZING HEALTHCARE SERVICES CONSUMPTION

RELATED APPLICATIONS

This application is a continuation of and claims priority to U.S. patent application Ser. No. 16/405,408, filed May 7, 2019, entitled "Method of Optimizing Healthcare Services Consumption," which is a continuation of and claims priority to U.S. patent application Ser. No. 15/584,664, filed May 2, 2017 entitled "Method of Optimizing Healthcare Services Consumption," which is a continuation of and claims priority to U.S. patent application Ser. No. 14/278,750, filed May 15, 2014 entitled "Method of Optimizing Healthcare Services Consumption" (abandoned) and U.S. patent application Ser. No. 14/278,733, filed May 15, 2014 entitled "Method of Optimizing Healthcare Services Consumption" (abandoned), which are continuations of and claim priority to U.S. patent application Ser. No. 13/742,625, filed Jan. 16, 2013 entitled "Method of Optimizing Healthcare Services Consumption" (abandoned), which is a continuation of and claims priority to U.S. patent application Ser. No. 13/178,174, filed Jul. 7, 2011, now U.S. Pat. No. 8,489,420 entitled "Method of Optimizing Healthcare Services Consumption," which is a continuation of and claims priority to U.S. patent application Ser. No. 12/773,334, filed May 4, 2010, now U.S. Pat. No. 8,036,916 entitled "Method of Optimizing Healthcare Services Consumption," which is a continuation of and claims priority to U.S. patent application Ser. No. 10/313,370, filed Dec. 6, 2002, now U.S. Pat. No. 7,711,577 entitled "Method of Optimizing Healthcare Services Consumption," the entire disclosures of which are expressly incorporated herein by reference.

FIELD OF THE INVENTION

The present invention generally relates to a method of optimizing healthcare services consumed by patients including employees and their family members by improving the overall quality of care and reducing the overall cost incurred by the employer, and more particularly to a method for application by a healthcare quality management firm (HQM) of characterizing the healthcare situation of an employer who pays for healthcare, comparing that healthcare situation to that of a geographic area in which the employer resides, identifying factors affecting the quality and cost of the healthcare, and recommending action for addressing the factors by applying resources at levels corresponding to the relative affect of the factors on the quality and cost of the healthcare.

BACKGROUND OF THE INVENTION

Employer sponsored healthcare benefits are of tremendous value to employees and their families. Such benefits, on the other hand, typically constitute a significant portion of an employer's total operating costs. Unfortunately, as medical costs continue to increase, the cost of providing employer sponsored healthcare benefits will continue to increase.

Currently, many employers attempt to offset the rising costs of providing healthcare benefits by shifting the cost to employees. Of course, only so much of the expense can be shifted to employees. At some point, the cost incurred by the employees will become prohibitive, and employer sponsored healthcare will no longer be seen as a benefit. Some employers attempt to monitor the price of certain healthcare services, but without information relating to the quality of the services, cost information is of limited value. Other employers have attempted to reduce their healthcare expenses by sponsoring health fairs or wellness screenings. This approach, while somewhat effective in prompting preventative healthcare, is not a focused expenditure of resources. For the majority of employees who are healthy, the money spent on wellness screenings is essentially wasted. Finally, employers sometimes attempt to negotiate the fixed costs associated with administering healthcare benefits. Again, since these costs typically make up only a small portion of the total cost, even successful negotiation attempts will have a limited impact on the employer's bottom line.

In short, employers have been largely unsuccessful in their attempts to control healthcare costs while ensuring a high level of care. Employers simply lack the information necessary to identify the most significant factors affecting their healthcare costs, to quantify and compare the performance of healthcare providers, and to apply their resources in a way that most effectively reduces both the overall consumption of healthcare and the costs of the services consumed while maintaining or improving the quality of the healthcare benefits they provide.

SUMMARY OF THE INVENTION

The present invention provides a method of optimizing healthcare services consumption through analysis of the demographic and wellness characteristics of an employee population (including employees and employee family members, hereinafter, "patients"), analysis of the quality and cost efficiency of the practices of providers used by the patients, and intervention with patients and providers to improve the overall health of the patients, the practices of the providers, and the cost efficiency of the employer provided healthcare plan. The method, in one embodiment thereof, includes the steps of assessing the healthcare situation of the employer as it relates to normative characteristics of a health economic zone including the patients, identifying patients from the covered population likely to generate expensive healthcare claims relative to the other patients based on data representing past healthcare claims generated by the patients, periodically determining whether these patients have obtained healthcare services that satisfy predetermined requirements, identifying qualified providers in the health economic zone who provide high quality, cost efficient healthcare services relative to other providers in the health economic zone based on data representing past practice patterns of the providers, prompting patients who have not obtained healthcare services that satisfy the predetermined requirements to obtain additional healthcare services from the qualified providers, and responding to healthcare requests from patients by determining whether the requesting patient is seeking to obtain healthcare services from a qualified provider, and, if not, urging the patient to obtain services from a qualified provider.

The features and advantages of the present invention described above, as well as additional features and advantages, will be readily apparent to those skilled in the art upon reference to the following description and the accompanying drawings.

BRIEF DESCRIPTION OF THE DRAWINGS

FIGS. 5-15 are illustrations of reports generated according to an embodiment of the present invention.

DETAILED DESCRIPTION OF EMBODIMENTS OF THE INVENTION

The embodiments described below are merely exemplary and are not intended to limit the invention to the precise forms disclosed. Instead, the embodiments were selected for description to enable one of ordinary skill in the art to practice the invention.

Figure 1:
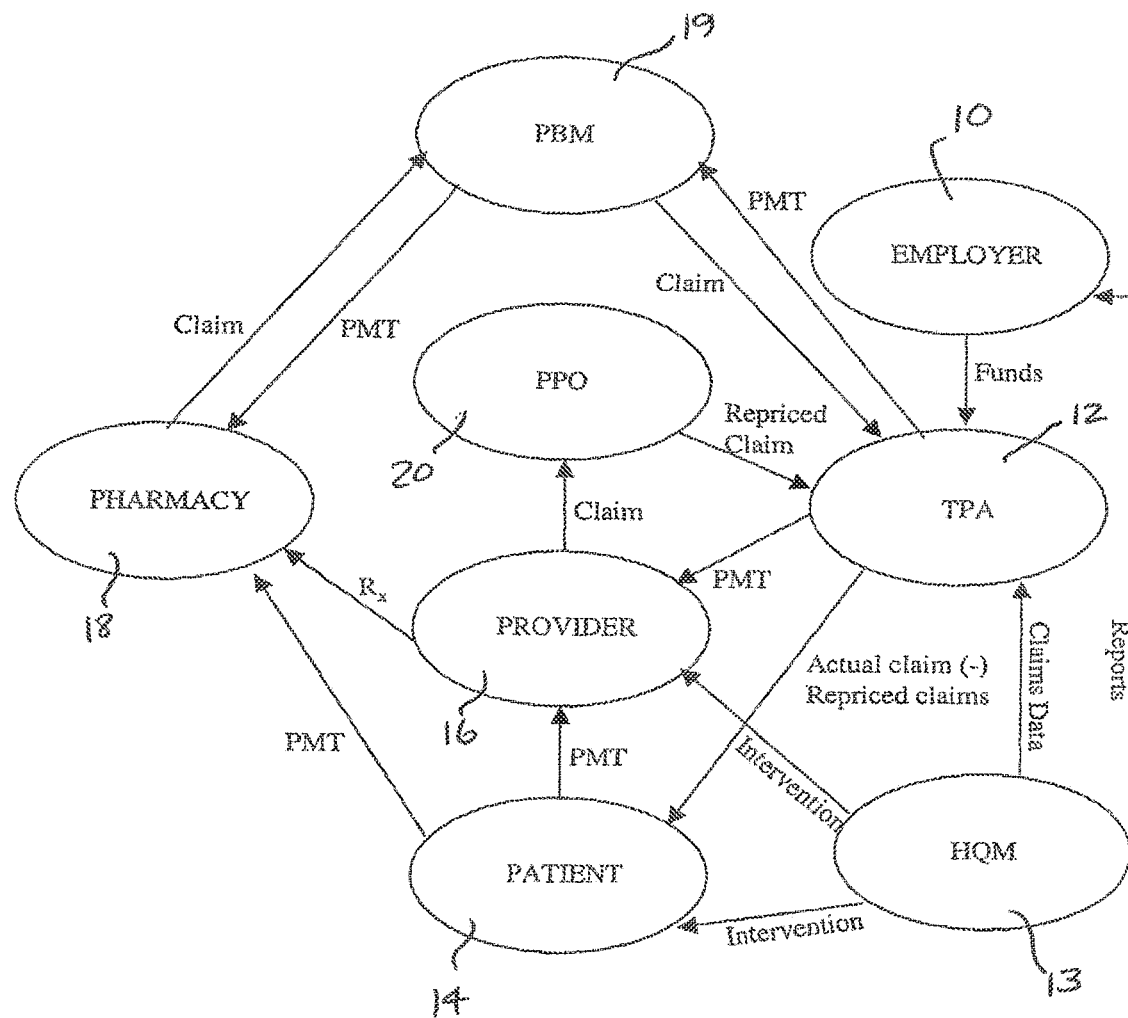
FIG. 1 is a conceptual diagram of participants in a healthcare consumption situation that may be optimized using a method according to the present invention.

FIG. 1 depicts a relationship among participants in a typical employer provided healthcare situation. In this example, the employer 10 is self-insured and provides funds, based on predicted healthcare costs, to a third party administrator (TPA 12) of healthcare benefits for paying employee healthcare claims. Of course, also involved in this relationship are the healthcare consumer, patient 14, the healthcare provider 16 (e.g., a physician or a facility such as a hospital, laboratory, etc.), a pharmacy 18, a pharmacy benefit manager (PBM 19), a PPO 20, and a healthcare quality management firm (HQM 13). As should become apparent from the following description, HQM 13 could perform the functions of TPA 12. Thus, except where expressly indicated otherwise or mandated by the context of this description, references to HQM 13 may include HQM 13 and TPA 12.

In a typical transaction associated with a healthcare claim, patient 14 visits provider 16 to obtain healthcare services and/or products such as drugs. For simplicity, this description collectively refers to services and products as healthcare services. Provider 16 submits a claim to PPO 20 (or alternatively directly to TPA 12) in an amount corresponding to the cost of the services. Provider 16 may also write a prescription that is received by a pharmacy 18. In that event, pharmacy 18 submits a claim to PBM 19, which in turn submits a claim to TPA 12. As is well known in the art, PPO 20 (or alternatively TPA 12) typically discounts or reprices the claimed charges based on an agreement between provider 16, pharmacy 18, and PPO 20. The repriced claim is submitted to TPA 12 for payment. TPA 12 accesses funds in the healthcare account of employer 10 to pay provider 16 and PBM 19 the repriced claim amounts. PBM 19 then forwards a payment to pharmacy 18. TPA 12 then also informs patient 14 of the patient's payment responsibility that arises as a part of the application of the terms of the underlying benefit plan when it does not pay 100% of eligible charges. Patient 14 then sends a payment to provider 16. The above-described example assumes that TPA 12 is separate from HQM 13. If HQM 13 functions as a combination of HQM 13 and TPA 12, then HQM 13 interacts directly with employer 10, patient 14, provider 16, PBM 19, and PPO 20 in the manner described with reference to TPA 12 above.

As should be apparent from the foregoing, throughout each such transaction, TPA 12 has access to all of the material claim information. TPA 12 shares this information with HQM 13, which may contact employer 10, patient 14, and/or provider 16. Accordingly, as will be described in detail below, HQM 13 is in a position to facilitate change in and/or directly influence the healthcare situation to control the cost incurred by employer 10 and to encourage consumption of healthcare from high quality providers 16. Thus, HQM 13 is described below as practicing the present invention as a service for the benefit of its clients, employers 10, and patients 14 including the clients' employees and their family members.

Figure 2:
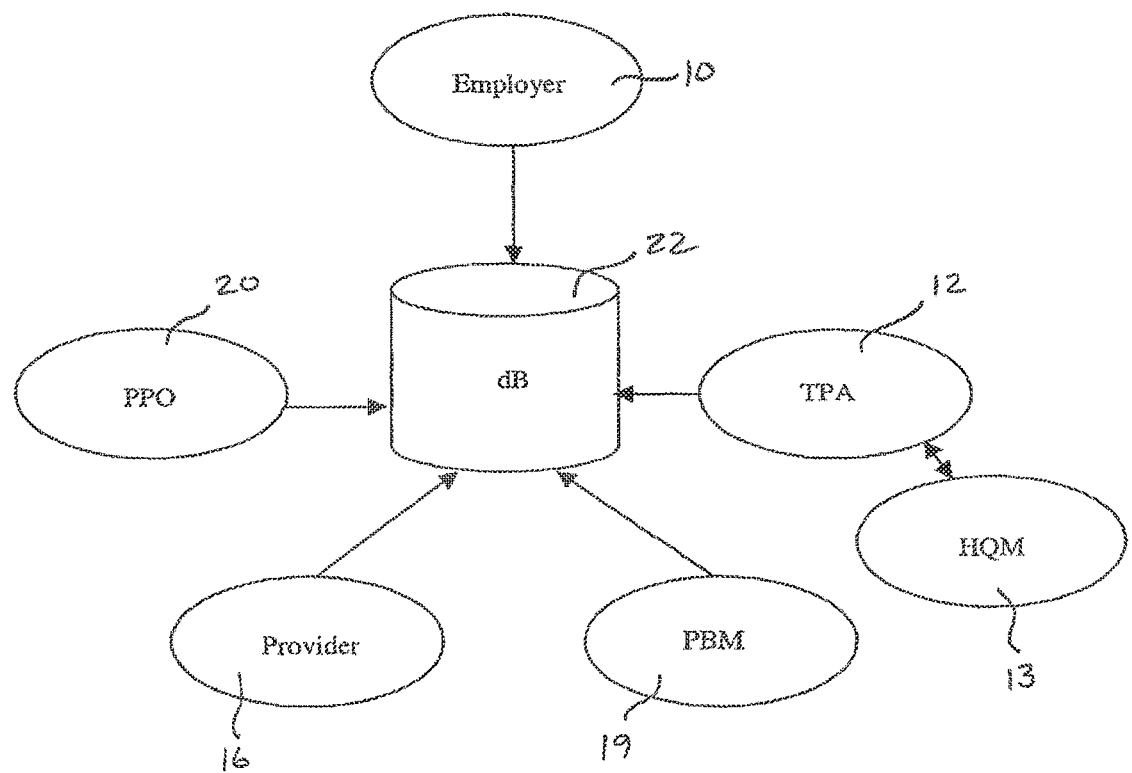
FIG. 2 is a conceptual diagram of an interrelationship between a central database and the participants shown in FIG. 1.

According to one embodiment of the present invention, TPA 12 maintains a database 22 including a variety of different types of information from employer 10, provider 16, PBM 19, and PPO 20 as depicted in FIG. 2. As is further described below, TPA 12 also updates information included in database 22 as a result of its interaction with HQM 13. Database 22 may be maintained on any of a variety of suitable computer-readable media such as a hard drive of a computer. While FIG. 2 suggests contributions of information to database 22 by each of employer 10, TPA 12, provider 16, PBM 19, and PPO 20, it should be understood that such information may not be provided directly to database 22. Instead, TPA 12 may receive information from the other participants and enter and/or otherwise process the information for storage in database 22. For example, information may be transferred electronically from employer 10, provider 16, PBM 19, PPO 20, and HQM 13 to TPA 12 via a network or multiple networks. Moreover, TPA 12 may physically reside at multiple locations, each of which receives information from the other participants. Such multiple locations may be connected together via a network configured to permit simultaneous access to database 22 through a server. Any suitable method of transferring information and storing such information in either a centralized or distributed database 22 is within the scope of the invention. For simplicity, the transfer of information is described herein as occurring electronically over a network, and database 22 is described as a centralized database accessible by a single TPA 12 location.

As is further described below, the information stored in database 22 permits HQM 13 to evaluate the healthcare situation of employer 10, including the cost information, the healthcare characteristics of patients 14, and the performance of providers 16 used by patients 14 covered under the healthcare plan provided by employer 10.

Accordingly, the information in database 22 includes employer information, patient information, provider information, pharmacy information, and claims information that may relate to some or all of the other types of information. The employer information includes information identifying employer 10, patients 14 covered under the employer provided healthcare plan, PPO 20 associated with employer 10, as well as historical data that characterizes changes in the healthcare situation of employer 10 over time. The patient information includes the name, address, social security number, age, and sex of each patient 14 covered under the healthcare plan provided by employer 10. The provider information includes the name, tax identification number, address, and specialty of a plurality of healthcare providers across a large geographic region, such as the entire United States. As is further described below, portions of the provider 10 information are associated with employer 10. These portions correspond to the providers 16 that provide services to patients 14. The pharmacy data includes information identifying the type, quantity, and dosage of drugs associated with a particular prescription for a particular patient 14 as well as the social security number of the patient 14. This information permits association of prescription drug claims with patients 14. These claims can be further associated with the provider 16 that wrote the prescription by accessing the claims data (described below) associated with the patient 14 who filled the prescription to determine which provider 16 patient 14 saw prior to obtaining the prescription. Alternatively, an identifier may be included in the pharmacy data with each prescription entry that identifies provider 16.

The claims data stored in database 22 include portions of the above-described data, but may be organized or associated with a particular claim. More specifically, a claim may include information identifying and/or describing employer 10, patient 14, provider 16, pharmacy 18, PBM 19, and PPO 20. The claim may further include information describing the condition or symptoms of patient 14 that generated the claim, the diagnosis of provider 16, the procedures ordered by provider 16 to treat the diagnosed condition as identified by commonly used procedure codes, and the costs (both original charges and repriced amounts) of the healthcare services associated with the claim.

As indicated above, the information stored in database 22 comes from a variety of sources. For example, when an employer 10 becomes a new client of HQM 13, PPO 20 servicing employer 10 may provide HQM 13 with enrollment data including employer information, employee information, and associated past claims information. HQM 13 may then process that information for addition to database 22. Periodically, PPOs 20 of employers 10 transfer claims information to TPA 12 (i.e., as the claims information is processed by PPOs 20). As indicated above, in addition to information relating to associated healthcare services, this claims information may include employee information, provider information, and pharmacy information. Additionally, PBMs 19 (or data transfer services working with PBMs 19) periodically transfer pharmacy information to TPA 12. As further described below, each time new information is provided to TPA 12, TPA 12 and/or HQM 13 may process the information such that it is associated with a particular employer 10, a particular patient 14, or a particular provider 16.

Figure 3:
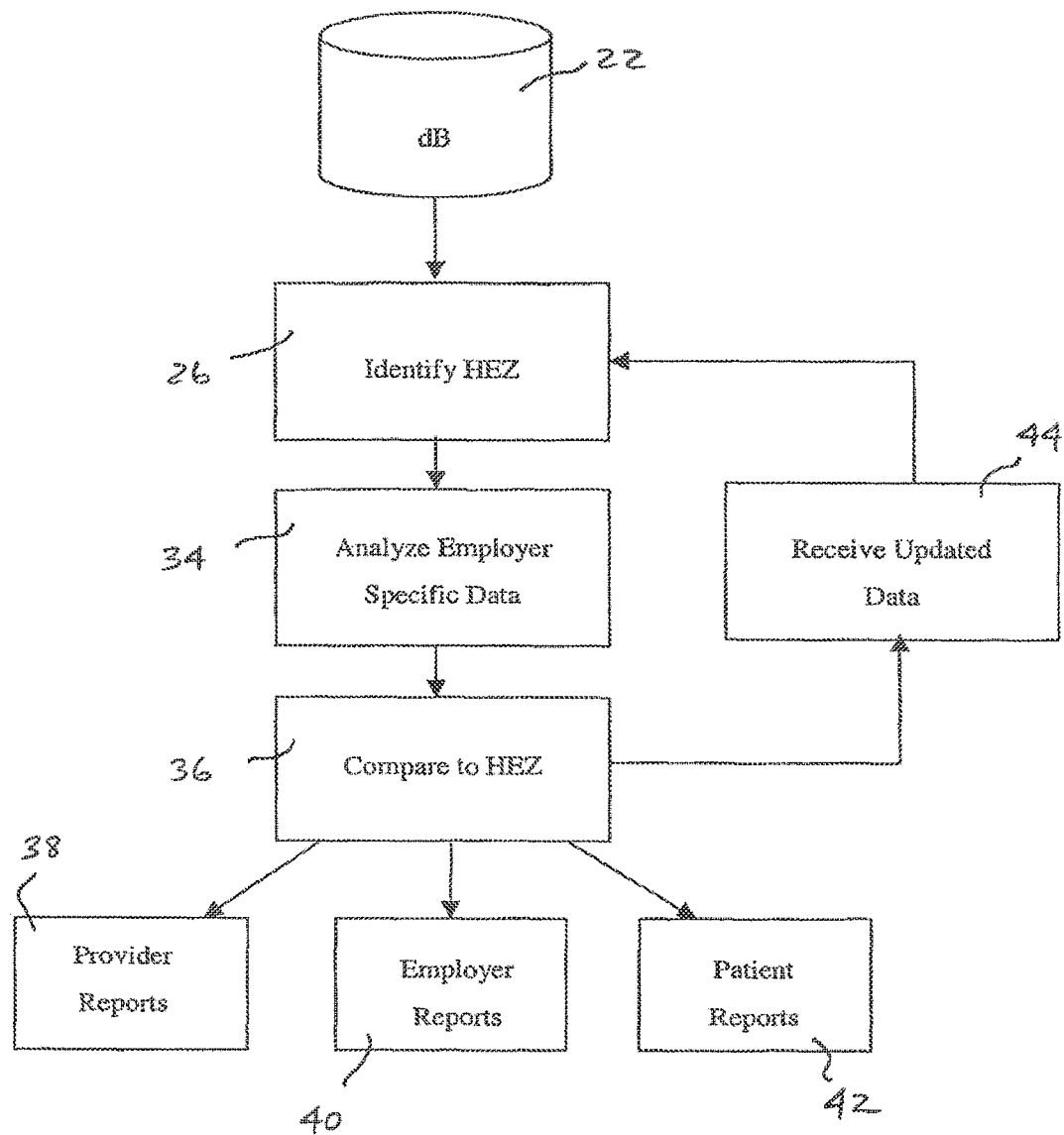
FIG. 3 is a flow diagram depicting steps included in one embodiment of the present invention.
Figure 4:
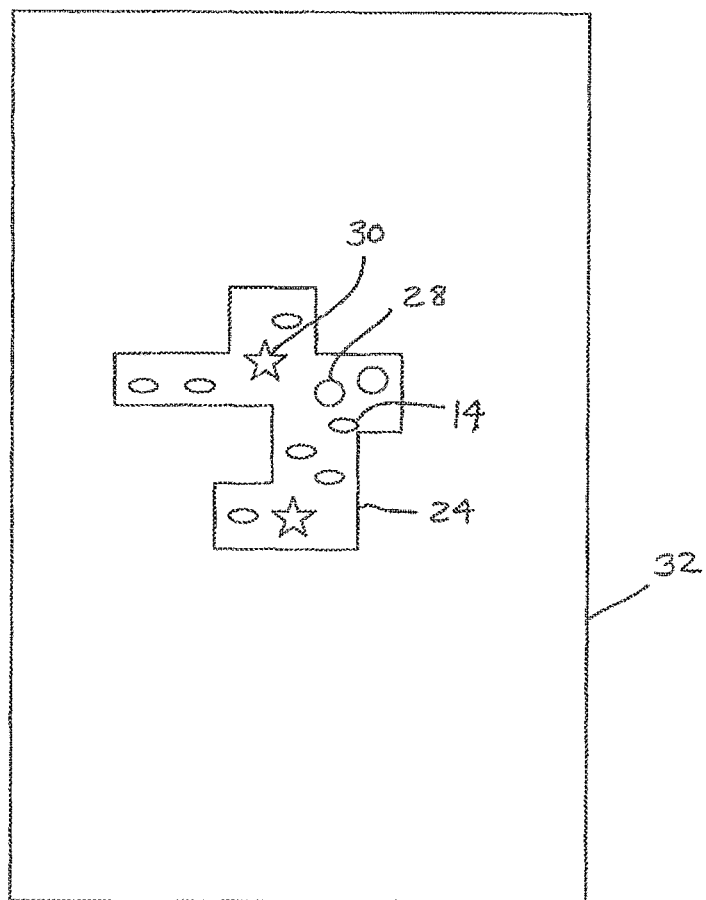
FIG. 4 is a conceptual diagram of a health economic zone.

Referring now to FIGS. 3 and 4, one embodiment of the method according to the present invention may be generally described as involving three basic steps: analyzing the healthcare situation of employer 10, improving the healthcare consumption characteristizcs of patients 14, and improving the overall performance characteristics of providers 16 used by patients 14. One process for analyzing a healthcare situation of an employer 10 is depicted in FIG. 3. In general, after all of the relevant information regarding employer 10, patients 14 associated with employer 10, and providers 16 used by patients 14 resides in database 22, HQM 13 executes software (as further described below) to access database 22 and identify a Healthcare Economic Zone (HEZ 24, FIG. 4) corresponding to employer 10 (step 26). As shown in FIG. 4, HEZ 24 corresponds to a geographic area that includes all patients 14 associated with all employers 10 and providers 16 used by patients 14 (including physicians 28 and facilities 30, such as hospitals). HEZ 24 may be defined to correspond to Hospital Service Areas set forth by the Dartmouth Atlas project, a funded research effort of the faculty of the Center for the Evaluative Clinical Sciences at Dartmouth Medical School. Essentially, HEZs are based on the zip codes of the residential addresses of patients 14 stored in database 22 and the locations of providers 16 servicing those zip codes. In other words, an HEZ 24 includes a geographic region in which patients 14 tend to obtain their primary healthcare. For example, assuming patients 14 associated with employer 10 all reside in three adjacent zip codes that are serviced by one facility 30 (also within one of the three zip codes), then those three zip codes are included in HEZ 24. However, if facility 30 also refers patients 14 to, for example, specialist providers 16 in a fourth zip code, then the fourth zip code is also included in HEZ 24. FIG. 4 shows HEZ 24 fully contained within a larger geographic area such as a state 32. It should be understood, however, that HEZs 24 (or the equivalent of HEZs 24) may extend across state lines.

Referring again to FIG. 3, step 34 indicates that information in database 22 corresponding to employer 10 (i.e., employer information, patient information, claims information corresponding to patients 14 associated with employer 10, and provider information) is analyzed to evaluate the healthcare situation of employer 10. In step 36, the employer specific data is compared to generalized data relating to HEZ 24 as is further described below. As indicated in FIG. 3, the results of the analyses performed in steps 26, 34, and 36 may be processed in the form of provider reports 38, employer reports 40, and patient reports 42, some or all of which may be provided to employer 10 as shown in FIG. 1 as part of the process of analyzing the healthcare situation of employer 10. Step 44 depicts the process of updating database 22 as HQM 13 and/or TPA 12 receive claims information and/or changes in the population of patients 14 associated with employer 10 as a result of employees being hired by or departing from employer 10, or changes in the family situation of the employees. As should be apparent from the figure, the process of analyzing the healthcare situation of employer 10 is therefore continuously updated and may result in generation of periodic reports for employer 10 and HQM 13 to track changes in the healthcare situation over time.

FIG. 5 depicts an example of an employer report 40. Although chart 46 of FIG. 5 does not compare employer 10 information to HEZ 24 information, it is an employer report 40 because it provides employer 10 information regarding the costs of healthcare services in the HEZ 24 in which employer 10 (more accurately, patients 14 associated with employer 10) resides. Chart 46 includes a specialty column 48, a total allowed charges column 50, a total allowed charges at normative costs column 52, a percent of excess charges column 54, and an excess charge per life per year column 56. Chart 46 provides employer 10 information regarding the relative costs of healthcare services (by specialty) in the employer's HEZ 24 as compared to the costs in a larger geographic area that includes HEZ 24 (e.g., state 32, the Midwest, the southeast, etc.). In this example, providers 16 in HEZ 24 charged $4,251,526 (column 50) for cardiology services over the course of a predetermined time period, such as two years. Column 52 shows that the normative costs for such services is $4,488,559 for the same number of healthcare consumers (i.e., patients 14) over the same predetermined time period. More specifically, the dollar amounts in column 52 are derived by first adding all of the charges for cardiology services in the larger geographic area for the predetermined time period and dividing the total by the number of healthcare consumers in the larger geographic area. Then, this "average cardiology charge per healthcare consumer" is multiplied by the number of healthcare consumers in HEZ 24. As shown in column 54, HEZ 24 experienced cardiology costs that were 5.3 percent below the normative cardiology charges. Finally, column 56 simply converts the percentage deviation from the normative charge into a dollar value divided by the number of healthcare consumers in HEZ 24 and the number of years in the predetermined time period.

Line 58 shows the totals for all specialties or Major Practice Categories (MPCs). Lines 60 and 62 illustrate a situation wherein HEZ 24 is serviced by more than one PPO 20. Since all of the claims information in database 22 is associated with a particular PPO 20, the charges associated with all claims of healthcare consumers in HEZ 24 corresponding to PPO network A and PPO network B may be separated based on the PPO that handled the claim. Thus, lines 60 and 62 depict the relative usage of the PPOs by healthcare consumers in HEZ 24 (column 50), the normative usage values for each PPO in a larger geographic area (eg., state 32) (column 52), the cost performance of the PPOs for HEZ 24 relative to the cost performance of the PPOs across state 32 (column 54), and the meaning of that relative performance on a dollars per patient 14 per year basis (column 56). Lines 64 and 66 provide similar information for two hospitals used by healthcare consumers in HEZ 24.

As should be apparent from the foregoing, employer 10 may readily scan down total allowed charges column 50 to determine the specialties most likely to contribute significantly to the employer's overall healthcare costs. Columns 54 and 56 permit employer 10 to readily identify those practice categories having charges that deviate most from the average or normative charges. In this manner, employer 10 (and HOM 13) can isolate the practice categories that have the most potential for providing the most significant reduction in the overall healthcare costs of employer 10.

Another employer report 40 (chart 68 of FIG. 6) follows the same format as chart 46, but compares the actual healthcare costs of employer 10 to the typical costs in HEZ 24. Chart 68 includes a specialty column 70, a total costs column 72, a normalized costs in HEZ 24 column 74, a percent excess column 76, and an excess cost per life per year column 78. Column 72 represents the total costs employer 10 incurred for the various specialties listed in column 70 during a predetermined time period. The normalized amounts in column 74 represent the expected cost in HEZ 24 for an employer having the same number of patients 14 as are associated with employer 10. For example, assuming a total cost for cardiology in HEZ 24 of $17,122,789 for 35,623 healthcare consumers in HEZ 24, the average cardiology cost per healthcare consumer is $480.67. Assuming that employer 10 has 150 patients 14, then the expected total cost for cardiology services (i.e., the normalized costs in HEZ 24, column 74) is $72,100. Accordingly, employer 10 has incurred costs for cardiology services that are 23.7% below the anticipated amount for an employer the size of employer 10 located in HEZ 24 as shown by column 76. Column 78 reflects this percentage in a per patient 14 per year dollar value.

As should be apparent from the foregoing, chart 68 could readily be revised to reflect similar information for actual consumers of the particular specialties as opposed to patients 14 and healthcare consumers generally. In other words, if only nine patients 14 used cardiology services over the predetermined time period (resulting in a total cost of $55,000), column 74 could be modified to reflect the expected amount for nine of the average consumers of cardiology services in HEZ 24 over the predetermined time period. Of course, columns 76 and 78 would then reflect the difference between these values on a percentage and per life per year basis, respectively.

FIG. 7 is another employer report 40 that summarizes the illness burden and demographics of HEZ 24 associated with employer 10. Chart 80 includes a description column 82, an HEZ 24 data column 84, a normative value a larger geographic area including column 86 for HEZ 24, a percent excess column 88, and an excess per life per year column 90. It is well known that healthcare consumption is greater for adults verses children (other than newborn children), for females verses males, and for older adults verses younger adults. Obviously, healthcare consumption is also greater for individuals having certain types of pre-existing illnesses as compared to healthy individuals. The method of the present invention uses these factors to compute a healthcare index (line 92 in FIG. 7) for HEZ 24 in which patients 14 associated with employer 10 reside. The method of the present invention calculates the healthcare index for an HEZ 24 using Episode Risk Group (ERG) scores inherent in the health risk assessment process provided by Symmetry Health Data Systems, Inc. and described in "A New Approach to Health Risk Assessment," a white paper available from Symmetry Health Data Systems, Inc., the disclosure of which is hereby incorporated herein by reference. A healthcare index for each patient 14 in HEZ 24 is computed using a retrospective analysis, and the index for HEZ 24 is derived by calculating an average index for all patients 14 in HEZ 24. As shown in column 84 of FIG. 7, HEZ 24 has 9,808 patients 14 having an average age of 42, and comprising 74.8% adults, 38.6% of whom are female. These factors result in a healthcare index for HEZ 24 of 1.506. As shown in column 88, this healthcare index is 50.6% above the normative healthcare index of 1.0 for the larger geographic area. This high healthcare index results from a higher than typical percentage of females and adults in HEZ 24 and a higher than typical percentage of individuals with health risk factors. More specifically, as shown in column 88 of FIG. 7, 10.8% of the overage is due to atypical demographics (i.e., an older and more heavily female population). 39.8% of the overage is due to the atypical illness burden of the population (i.e., a population with health conditions corresponding to higher than typical health risk factors). Accordingly, an employer 10 in HEZ 24 should expect to have healthcare costs that are greater than the typical costs of the larger geographic region. It should be understood that a similar report could readily be generated comparing the illness burden and demographic information of a particular employer 10 to information describing the HEZ 24 in which patients 14 associated with employer 10 reside.

Referring now to FIG. 8, a patient report 42 is shown summarizing the chronic illnesses of patients 14 associated with employer 10. It is well known that typically 80% of an employer's healthcare costs are generated by approximately 20% of the covered population of patients 14. That 20% of the population generally has a high incidence of chronic illness. Accordingly, chart 94 of FIG. 8 is generated to provide employer 10 a summary of its chronically ill patients 14.

As shown, column 96 lists various chronic illnesses. While the method of the present invention may track any number of chronic illnesses, only six are shown in FIG. 8. Column 98 shows the number of patients 14 having each of the listed illnesses. Column 100 shows the number of those patients 14 listed in column 98 that have at least one year of claims history (i.e., have submitted claims that were added to database 22). Column 102 shows the number of patients 14 that have satisfied the minimum annual care requirements (MACRs) recommended for treating the chronic illness or illnesses from which they suffer. Column 104 simply expresses the number in column 102 in the form of a percentage of the total patients 14 suffering from the listed illness. The MACRs for each chronic illness of chart 94 are listed in column 106 and obtained using software available from McKesson Corp., a supplier of information and managed care products and services for the health care industry. In particular, McKesson's CareEnhance Resource Management Software (CRMS) provides such information. As the method of optimizing healthcare services consumption described below is practiced, periodic reports such as chart 94 of FIG. 8 will show improvements in the number of patients 14 that satisfy the MACRs associated with their particular illness(es).

Chart 110 of FIG. 9 shows the chronic illness status of patients 14 associated with employer 10 in terms of co-morbidities. Chart 110 includes a description column 112, a current patient column 114, a percent of current covered patients column 116, a previous patient column 118, a percent of previous covered patients column 120, and a percent of database driven norms column 122. As shown in column 114, of the 993 total patients 14 covered under a healthcare plan provided by employer 10, a total of 619 have a single chronic illness, 236 have two chronic illnesses, 86 have three chronic illnesses, etc. Column 116 expresses the number of patients 14 listed in column 114 in terms of the percentage of the total patient 14 population. Columns 118 and 120 include similar information representing the status of the chronically ill at a previous date. Employer 10 can monitor changes in the chronic illness status of its patients 14 by comparing these two sets of columns. Finally, column 122 shows the typical percentage of individuals (based on all individuals reflected in the database) with the particular number of chronic illnesses.

In addition to summarizing patients 14 having chronic illnesses, the method of the present invention also includes the step of performing a risk stratification of all patients 14 covered by employer 10. The results of this risk stratification step are provided to employer 10 as an patient report 40. Chart 124 of FIG. 10 is an example of such an patient report 42. As shown, chart 124 includes a family identification number column 126, a patient identification column 128, an age column 130, a gender column 132, a healthcare index column 134, and a predicted cost column 136. The primary purpose of chart 124 is to display patients 14 in order of their associated healthcare index listed in column 134. The healthcare index is derived using the McKesson CRMS software as described above, which takes into account the age, gender, chronic illnesses, and co-morbidities of each patient 14. Also, by analyzing claims data describing prescriptions, the CRMS software imputes illnesses of patients 14 based on the number and types of medications prescribed for patients 14. Thus, the healthcare index is used to rank patients 14 in terms of their likelihood of generating large medical expenses in the near future. It should be noted that not only the chronically ill are identified by the healthcare index. Other patients 14 having conditions that are not considered chronic may have high healthcare indices. Column 136 provides a predicted cost associated with each patient 14 based on their healthcare index. More specifically, column 136 is derived by calculating the total expense associated with the normative population, and dividing that amount by the total number of ERG risk points of the normative population to get dollars per risk point (prospectively). Then, using the method of the present invention (and not the CRMS software), the healthcare index of column 134 is multiplied by the dollars per risk point value.

The above-described employer reports 40 and patient reports 42 are illustrative of the way in which the method of the present invention determines which patients 14 covered by employer 10 should receive intervention or proactive coaching (as further described below and depicted in FIG. 1), and at what level of intensity. In other words, since chronically ill patients 14 generally generate large healthcare costs, chronically ill patients 14 should be monitored and coached most actively and at levels corresponding to the number of chronic illnesses from which they suffer. Likewise, patients 14 having high healthcare indices because of their age, gender, illnesses, etc. should be monitored and coached most actively and at levels corresponding to their healthcare index. Using the above-described approach, patients 14 that require proactive coaching typically constitute approximately 25% of the total patient 14 population. It has been shown that this 25% portion of the patient 14 population typically generates 90% of the total healthcare costs incurred by employers 10.

Figure 11:
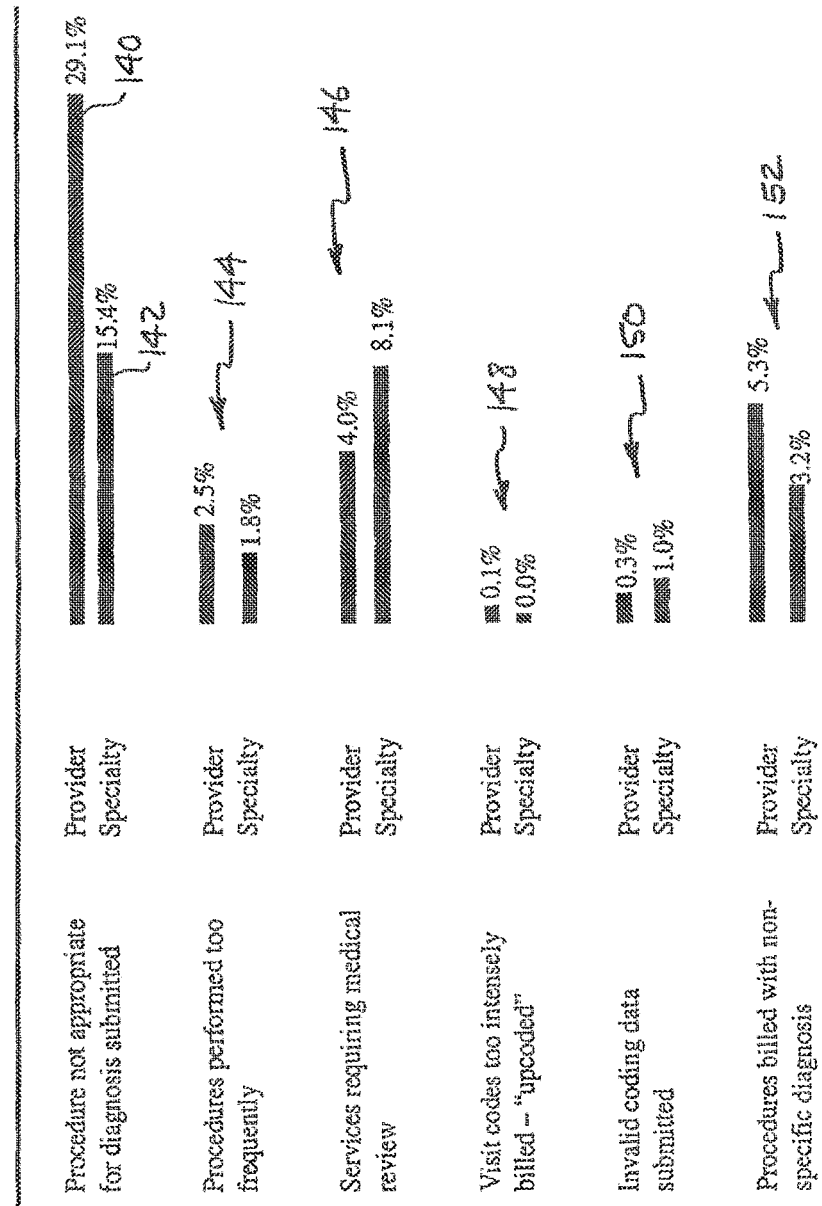

As indicated above, the method of the present invention also generates physician reports 38 such as chart 138 shown in FIG. 11. Chart 138 is an example of a comparison of various characteristics of the practice of a particular provider 16 to the practices of other providers 16 in the same specialty. In order to make such comparisons, the claims information in database 22 may be analyzed on the basis of "episodes" of healthcare. This analysis is performed using software applications available from McKesson Corp., which analyze the services and costs associated with claims originated by a particular provider 16. An episode is defined as a healthcare consumption sequence including all healthcare services consumed by a patient 14 for a particular healthcare problem. Episodes may include healthcare services ordered by a physician as a result of an initial office visit (e.g., tests, X-rays, etc.), healthcare services associated with a subsequent hospital visit (e.g., for surgery), and healthcare services associated with aftercare or follow-up visits to the physician.

The analysis of claims information grouped by specialty episodes permits identification of providers 16 having practice patterns that result in low total costs for the types of healthcare problems they treat as compared to other providers 16 in the specialty. Additionally, providers 16 who deliver high levels of post-primary preventative care services for chronically ill patients 14 can be identified. Finally, specific undesirable characteristics of a provider's 16 practice patterns can be identified such as up-coding, ordering inappropriate services, vague or invalid diagnostic codes, and services that are performed too frequently. All of this information is available from the 10 claims information stored in database 22.

Referring back to FIG. 11, Bar 140 of chart 138 represents the percentage of procedures ordered by a particular provider 16 (physician ID #223776) that were determined to be inappropriate for the diagnosis reflected in the claims information associated with the evaluated episodes. Bar 142 represents similar data for the entire specialty. Comparing bar 140 to bar 142 shows that this particular anesthesiologist ordered inappropriate procedures at nearly double the rate of others in the specialty. The remaining bar groups 144, 146, 148, 150, and 152 permit similar comparisons for the practice pattern characteristics indicated on chart 138.

As further described below, one of the steps of a method according to the present invention involves determining whether providers 16 used by employees 14 of employer 10 provide healthcare in a manner that satisfies certain criteria. If so, these providers 16 are identified as Quality Service Providers or QSPs. To achieve a QSP designation or rating, providers 16 must, based on claims information stored in database 22, pass three screens or quantitative tests of the providers' 16 performance or practice characteristics. Any provider 16 who fails one or more of these tests is identified for purposes of practicing the present invention as a non-certified QSP ("NCQSP").

Figure 12:
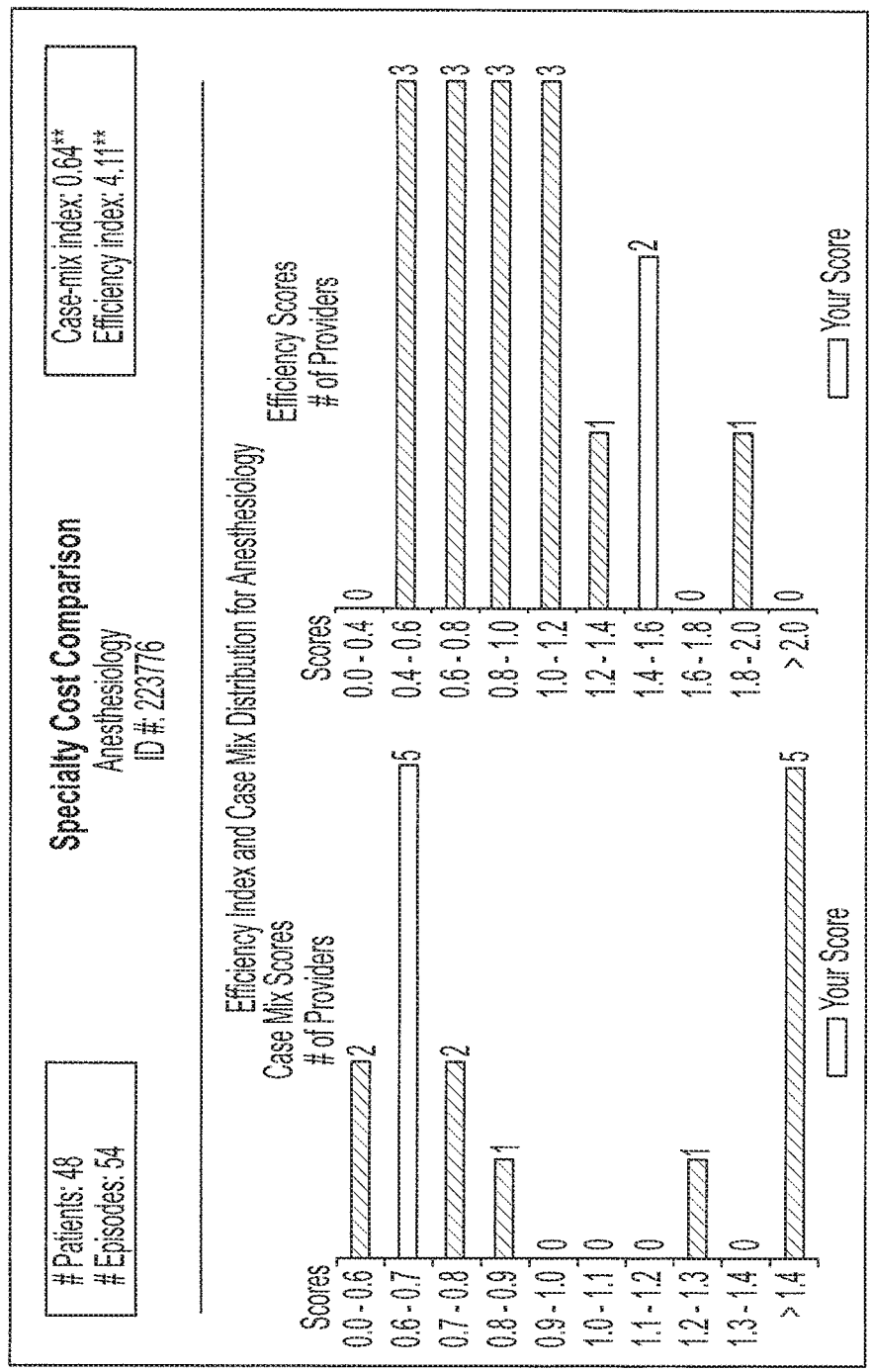

The first test ("the CEI test") is primarily economic. Using claims information in database 22, the software of the present invention generates a Cost Efficiency Index (CEI) for each provider 16. The CEI represents the actual total cost of care provided and/or ordered by provider 16 for completed episodes, divided by the total average cost of such care for similar episodes treated by other providers 16 in the specialty. In other words, the cost to employer 10 for the healthcare delivered and/or ordered by provider 16 for all completed episodes for all patients 14 is first extracted from the claims information in database 22. Then, the total cost for all similar episodes handled by all providers 16 tracked in database 22 is determined, and divided by the total number of episodes to arrive at an average cost per episode in the specialty. Finally, the average cost per episode for provider 16 is divided by the average cost per episode in the specialty to arrive at the CEI for provider 16. If provider 16 has a CEI that exceeds a predetermined threshold (e.g.,) 125% or more above that of others in the specialty of provider 16) and is statistically higher that the average for the specialty (i.e., sufficient claims information is contained in database 22 to calculate the CEI of provider 16 with a statistically acceptable confidence level such as at the p 0.1 level), then provider 16 failed the CEI test and will be designated a NCQSP. A sample report of the data used to complete a CEI analysis is shown in FIG. 12.

Figure 13:
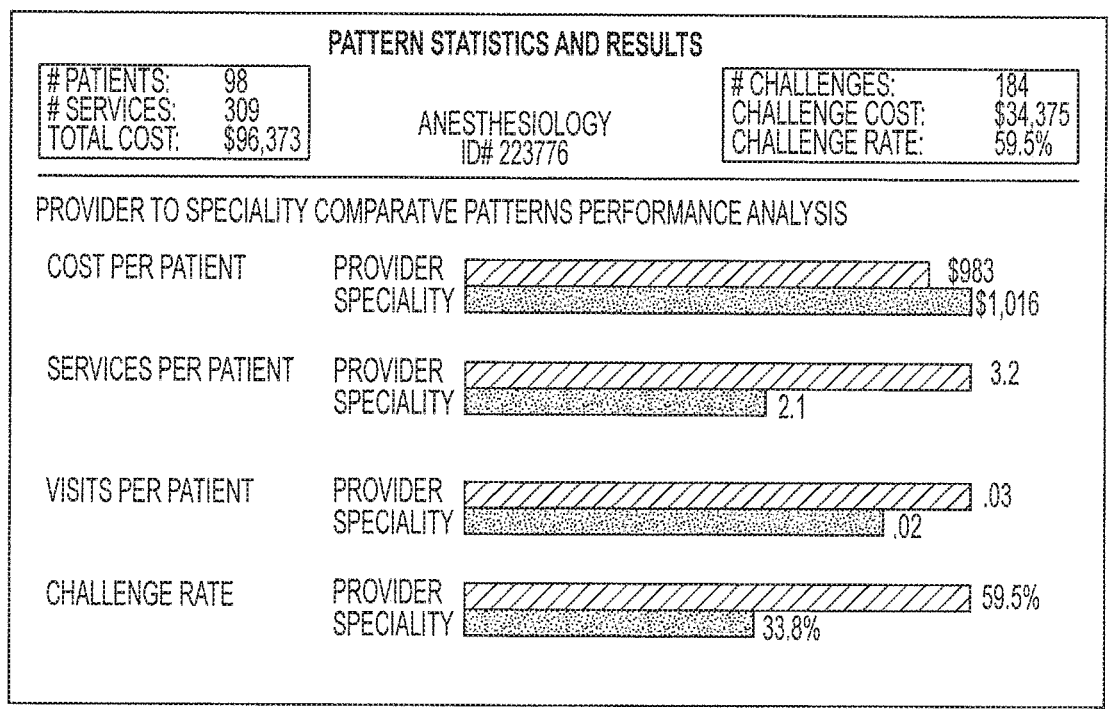

The second test in the QSP rating process ("the service rate test") evaluates the preventative care practices of providers 16. As is well known in the field of medical care, preventative care services may significantly affect the overall cost of healthcare, particularly those services provided to treat chronic illnesses to prevent those illnesses from progressing or resulting in other health complications. The McKesson software permits extraction of data representing the number and types of preventative care services ordered by providers 16 for treatment of chronic conditions. In one embodiment of the invention, nineteen chronic conditions are tracked. To evaluate a particular provider 16, the data representing the preventative care services for provider 16 is extracted and compared (according to the method of the present invention) to a minimum number and particular types of services considered acceptable in treatment of the particular chronic conditions treated by provider 16. This analysis results in a service rate for provider 16. More specifically, the total number of services ordered for chronically ill patients treated by provider 16 is determined, and then divided by the number of services required for such patients to achieve compliance with the associated MACRs. This service rate, or fraction of recommended MACRs, is then compared to the typical service rate in the appropriate specialty. If provider 16 has a service rate that is both less than a certain percentage of the typical service rate (e.g., has ordered 75% or less of the services required to achieve compliance with the associated MACRs) and statistically significantly lower than the average for the specialty (i.e., a statistically significant sample size is available in database 22 to obtain confidence at the p 0.1 level), then provider 16 failed the service rate test and is designated a NCQSP. A sample report representing the results of a service rate analysis is shown in FIG. 13.

Figure 14:
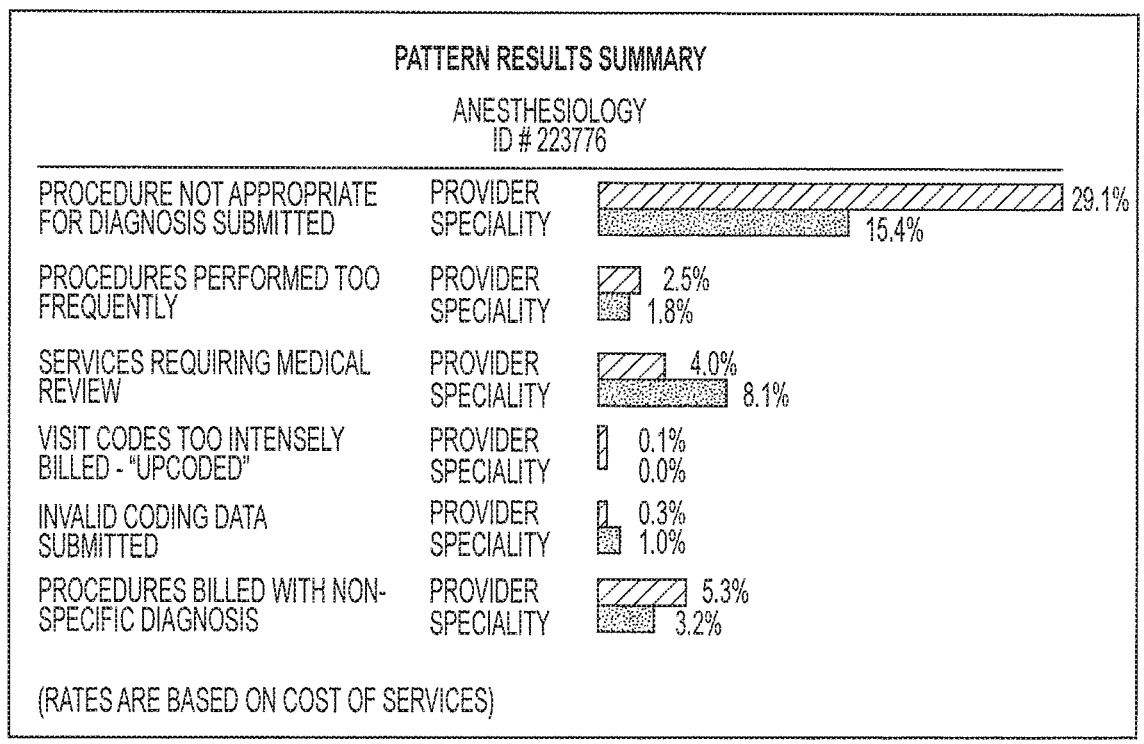

The third test (the "practice patterns test") involves an evaluation of the overall practice patterns of providers 16. More specifically, the McKesson clinical software is used to extract the number of occurrences of up-coding, ordering inappropriate services, vague or invalid diagnostic codes, and services that are performed too frequently, both for the particular provider 16 being evaluated, and for the specialty as a whole. Each practice pattern category is evaluated according to the method of the present invention to determine whether provider 16 practices in a manner that results in a practice patterns challenge rate that exceeds a predetermined multiple of the typical practice pattern percentages (e.g., 200% or more than the typical practice patterns) and is statistically significantly higher than the average percentages (e.g., at the p 0.01 level). If so, provider 16 failed the practice patterns test and is designated a NCQSP. A sample report representing the results of a practice patterns analysis is shown in FIG. 14.

According to the present invention, providers 16 that pass each of the three tests are assigned a QSP designation, indicating that providers 16 practice high quality medicine in a cost effective manner. As will be further described below, these QSP providers 16 are targeted by the present method for providing a maximum percentage of the overall healthcare consumed by patients 14 of employer 10. In addition to the basic QSP/NCQSP distinction resulting from the above-described process, providers 16 may be further ranked based on the results of the above-described tests. For example, the QSP category of providers 16 may be divided into "A" level QSP providers 16 and "B" level QSP providers 16. "A" level QSP providers 16 may be defined as providers 16 who have historical claims data in database 22 representing at least five episodes of the relevant type ("sufficient episodic data"), pass the CEI test with a CEI of less than 100% of the typical CEI in the specialty, and pass both the service rate test and the practice patterns test. "B" level QSP providers 16 may include providers 16 who (1) do not have sufficient episodic data, or (2) have sufficient episodic data and pass all three tests, but with a CEI of greater than or equal to 100% of the typical CEI in the specialty.

Similarly, providers 16 falling into the NCQSP category may be further ranked relative to one another to provide an ordered listing of NCQSPs. For example, "C" level NCQSP providers 16 may be defined as providers 16 who have sufficient episodic data, pass the CEI test, but fail one of the service rate or practice patterns tests (not both). "D" level NCQSP providers 16 may be defined as providers 16 who have sufficient episodic data and (1) fail the CEI test with a CEI of less than 150% of the typical CEI in the specialty or (2) fail both the service rate and practice patterns tests. Finally, an "E" level NCQSP provider 16 may be defined as a provider 16 with sufficient episodic data who fails the CEI test with a CEI that is at least 150% greater than the typical CEI in the specialty. Thus, providers 16 may be categorized in levels "A" through "E." This ranking permits targeting not only QSPs, but "A" level and "B" level QSPs, or NCQSPs that at least have the best relative rankings on the list of NCQSPs.

Another example provider report 38 is shown in FIG. 15. Chart 154 of FIG. 15 is a listing of NCQSPs in descending order. The group of columns collectively assigned reference designation 156 identifies the providers 16 by ID, name, and location. Column 158 lists the number of episodes in database 22 associated with each provider 16. Column 160 lists the above-described CEI for each listed provider 16. The greater the CEI listed in column 160, the more significant the provider's deviation from the practice patterns of other providers 16 in the specialty. Consequently, those providers 16 listed near the top of chart 154 will provide healthcare resulting in a greater cost to employer 10. In one embodiment of the invention, listings of NCQSPs such as chart 154 are divided into thirds for purposes of practicing the invention as further described below.

Figure 16:
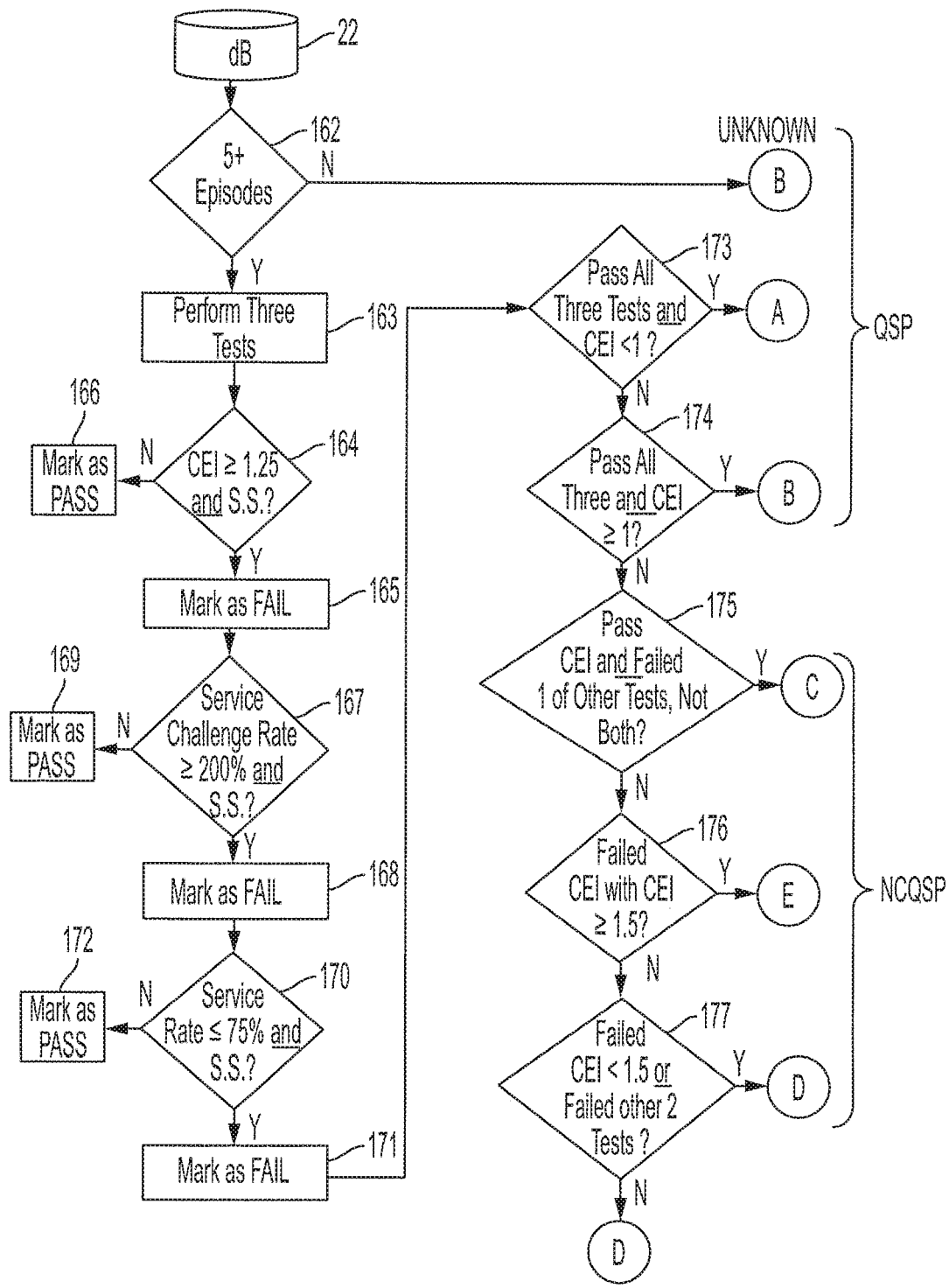
FIG. 16 is a flow diagram of a process for evaluating the practice characteristics of healthcare providers.

Referring now to FIG. 16, a flow diagram of the above-described process for assigning QSP or NCQSP designations to providers 16 is shown. At step 162, claims information corresponding to a particular provider 16 is extracted from database 22 to determine whether provider 16 has sufficient episodic data (e.g., at least five episodes of the relevant type). If not, then provider 16 is designated an unknown, "B" level QSP. If provider 16 has sufficient episodic data stored in database 22, then each of the three above-described tests are performed as indicated at step 163. At step 164, the results of the CEI test are analyzed. If the CEI is 125% or more greater than the typical CEI in the specialty and satisfies the above-described statistical significance criteria, then provider 16 is marked as failing the CEI test (step 165). Otherwise, provider 16 is marked as passing the CEI test (step 166). Similarly, the results of the practice patterns test are analyzed at step 167. If provider 16 has a service challenge rate of 200% or more than the typical rate in the specialty and satisfies the above-described statistical significance criteria, then provider 16 is marked as failing the practice patterns test (step 168). Otherwise, provider 16 is marked as passing the practice patterns test (step 169). Finally, the results of the service rate test are analyzed in a similar manner at step 170, and provider 16 is marked as failing (step 171) or passing (step 172) the service rate test as a result of the analysis.

As shown at step 173, "A" level QSPs are identified as providers 16 who are marked as passing all three tests and achieved a CEI of less than 1. If a provider 16 is marked as passing all three tests, but has a CEI that is greater than or equal to 1, then provider 16 is designated a "B" level QSP as indicated by step 174. The remaining providers 16 are NCQSP providers 16. At step 175, the method of the present invention identifies "C" level NCQSPs at step 176 as providers 16 who are marked as passing the CEI test, but failing one of the other two tests (but not both). At step 177, the lowest level providers 16 ("E" level NCQSPs) are identified as providers 16 who are marked as failing the CEI test with a CEI of at least 1.5. Any remaining providers 16 are designated "D" level NCQSPs as indicated at step 161. "D" level NCQSPs include providers 16 who are marked as failing the CEI test, but with a CEI of less than 1.5, and providers 16 who are marked as failing both the service rate and practice patterns tests. This process of evaluating providers 16 for purposes of determining QSP/NCQSP status and levels within each category is repeated periodically to maintain an updated listing in database 22. It should be further understood that the particular numeric threshold values used in each of the three tests may readily be changed to affect the number of providers 16 falling into each of the five levels without departing from the principles of the invention. The designations for providers 16 resulting from the above-described process are used to improve the quality and cost-efficiency of the healthcare services consumed by employees 14 of employer 10 in the manner described below.

Figure 17:
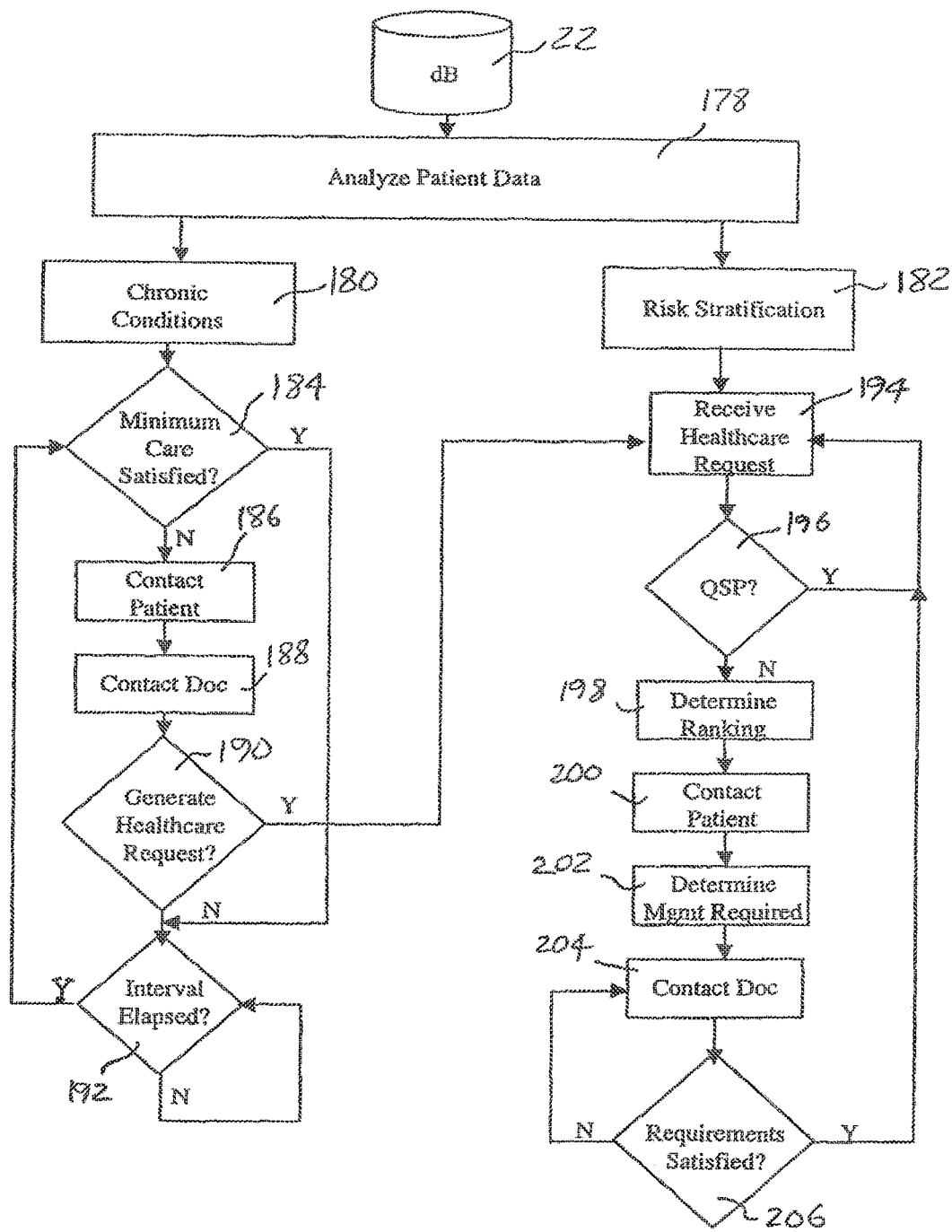
FIG. 17 is a flow diagram depicting steps included in one embodiment of the present invention.

Referring now to FIG. 17, a flow diagram representing a portion of a method for optimizing healthcare services consumption is provided. At step 178, the claims information corresponding to patients 14 is extracted from database 22. Step 178 results in the data necessary to identify patients 14 having chronic illnesses (step 180) and to rank patients 14 according to the above-described risk stratification process (step 182). As indicated above and shown in FIG. 1, the method of the present invention, in one form thereof, involves intervention with patients 14 by registered nurses and other staff of HQM 13. This intervention or proactive coaching follows one or both of the two paths depicted in FIG. 17. First, for patients 14 identified as having one or more chronic illness, the method of the invention determines at step 184, based on claims information associated with such patients 14, whether the MACRs associated with the illness(es) have been satisfied. If the MACRs for a particular patient 14 have not been satisfied, then a representative of HQM 13 (e.g., a registered nurse or other staff member) contacts patient 14 to remind patient 14 of the need to schedule the healthcare necessary to satisfy the MACRs. This contact may be accomplished by any mode of communication including by phone, email, fax, mail, or any combination thereof. Preferably, the representative of HQM 13 has a live conversation with patient 14 to impress upon patient 14 the importance of satisfying the MACRs associated with the patient's chronic illness.

At step 188, the representative of HQM 13 may also contact provider 16 of healthcare services associated with the chronic illness(es) of patient 14. As a result of this contact, the representative enlists the cooperation of provider 16 in the effort to persuade patient 14 to satisfy the MACRs. As should be apparent from the foregoing, a goal of this intervention is to improve the health of patient 14 and minimize the cost to employer 10 by avoiding the increased healthcare expenses typically accompanying untreated chronic illnesses.

Steps 186 and 188 may result in the generation of a healthcare request. Specifically, patient 14 may respond to contact by the representative of HQM 13 by scheduling an evaluation by provider 16 or other action toward satisfying the MACRs associated with the chronic illness(es) of employee 14. Step 190 represents the possibility that a healthcare request is generated. If so, the healthcare request is processed as described below with reference to the second path depicted in FIG. 17. Otherwise, a predetermined time period is allowed to pass before repeating the process of checking the compliance of patient 14 with the MACRs associated with the chronic illness(es) of patient 14 and contacting patient 14 and provider 16. Step 192 indicates this delay period.

When healthcare requests are generated, either as a result of the first path of FIG. 17 described above, or simply during the ordinary course of employee healthcare consumption, HQM 13 receives the healthcare request at step 194. The healthcare request is associated with a particular patient 14 based on the risk stratification process represented by step 182. By determining the risk ranking of the requesting patient 14, HQM 13 can perform intervention actions (as described herein) in the order of ranking of patients 14. In other words, since it is not possible to contact every patient 14 submitting a healthcare request, the ranking of patients 14 permits HQM 13 to focus first on patients 14 having a highest risk ranking, and then (time and resources permitting) patients 14 have a smaller likelihood of generating high cost healthcare claims. The method of the present invention next accesses database 22 to determine whether provider 16 associated with the healthcare request is currently designated a QSP according to the process described above. If patient 14 is requesting to obtain healthcare services from a QSP, then the healthcare request may be processed according to conventional procedures without intervention by representatives of HQM 13 as indicated by step 196. Alternatively, the QSPs resulting from the above-described evaluation process may be ranked relative to one another and categorized into, for example, the "A" and "B" level QSP classifications described above. In such an alternative embodiment, an additional step (not shown) between step 196 and step 194 of contacting an patient 14 requesting healthcare from a "B" level QSP may be provided. At that step, a representative of HQM 13 may attempt to influence patient 14 to obtain such services from a "A" level QSP.

If, on the other hand, the healthcare request seeks services from a NCQSP, then the ranking of the NCQSP (derived as explained above with reference to FIG. 16) is determined at step 198. At step 200, a representative of HQM 13 contacts patient 14 who generated the healthcare request to urge patient 14 to obtain the requested services from a QSP. The representative may explain to patient 14 that various other providers 16 within geographic proximity to patient 14 (determined in the manner described below) have achieved the QSP designation for high quality, cost efficient healthcare, while provider 16 selected by patient 14 has not achieved that designation. The representative may further explain the implications of obtaining healthcare services from NCQSPs, and attempt to assist patient 14 in rescheduling the requested healthcare services with a QSP. Additionally, if patient 14 refuses to switch to a QSP, the representative may attempt to persuade patient 14 to at least switch to a NCQSP that is ranked at a higher level than the currently selected NCQSP.

As described above, at step 200 of FIG. 14, the representative of HQM 13 may list for patient 14 the variety of other providers 16 (specifically, QSPs) within a specific geographic proximity to patient 14. Such a list is generated by accessing database 22 using a software interface configured to permit the HQM 13 representative to input a desired radius extending from the location of patient 14, thereby defining an area of geographic proximity surrounding patient 14. The software accesses database 22, identifies the QSPs located within the selected geographic area, and provides a listing to the HQM 13 representative. Using this software and method, the representative may access listings of QSPs within, for example, a five mile, ten mile, and/or fifteen mile radius of patient 14.

In the event patient 14 refuses to obtain healthcare services from a provider 16 other than the currently selected NCQSP, the method of the present invention determines (at step 202) the level of intervention required to minimize the costs of such services while maintaining high quality healthcare and the specific actions associated with that intervention level. A plurality of actions may be taken by the representative of TPA 12, depending upon the level of intervention required. As described above, the NCQSP listings generated by the present invention may, for example, be divided into thirds ("C," "D," and "E" level NCQSPs). "E" level NCQSPs require the greatest level of intervention because the healthcare provided by such NCQSPs, as evaluated by the three QSP tests described herein, most significantly deviates from characteristics associated with desirable healthcare services. "D" level NCQSPs require less intervention. Finally, providers 16 designated "C" level NCQSPs require the least intervention. This "stepped-down" approach to intervention permits efficient usage of the resources available to HQM 13 in managing the healthcare expenses of employer 10.

As indicated above, providers 16 at the top third of a NCQSP listing ("E" level NCQSPs) receive the highest level of monitoring and individual contact by representatives of HQM 13. If an "E" level NCQSP is identified at step 198 of FIG. 17, then step 202 obtains a listing of intervention actions associated with "E" level NCQSPs. These actions may include the following:

(1) Obtain criteria for any admission associated with the healthcare request, including medical history, tests, and lab work;
(2) Delay any admission for employee 14 until all days of admission are approved by an appropriate representative of HQM 13;
(3) Complete a telephone evaluation with the NCQSP provider 16, conducted by an appropriate HQM 13 representative, to evaluate and discuss the need for any admission;
(4) Review the need to continue an admission after each day of the admission;
(5) Delay any additional days of admission beyond the initial length of stay until such additional days are approved by an appropriate representative of HQM 13;
(6) Assign a representative of HQM 13 to provide assistance to provider 16 in determining appropriate services to address the healthcare problem and to report treatments proposed by provider 16 to an appropriate representative of HQM 13; and
(7) Contact provider 16 directly to discuss any questionable proposed treatments as determined by an appropriate representative of HQM 13.

If a "D" level NCQSP is identified at step 198 of FIG. 17, then step 202 obtains a listing of intervention actions associated with "D" level intervention. These actions may include the following:

(1) Obtain criteria for any admission associated with the healthcare request, including medical history, tests, and lab work;
(2) Assign a one-day length of stay and perform daily concurrent review of additional days, requiring approval by an appropriate representative of HQM 13 as needed;
(3) Require provider 16 to send notifications of admissions to an appropriate representative of HQM 13;
(4) Complete a telephone consultation with provider 16, conducted by an appropriate representative of HQM 13, if deemed necessary by the representative of HQM 13; and
(5) Assign a representative of HQM 13 to provide assistance to provider 16 in determining appropriate services to address the healthcare problem and to report treatments proposed by provider 16 to an appropriate representative of HQM 13.

Finally, if a "C" level NCQSP is identified at step 198 of FIG. 17, then step 202 obtains a listing of intervention actions associated with a "C" level intervention. These actions may include the following:

(1) Obtain criteria for any admission associated with the healthcare request, including medical history, tests, and lab work;
(2) Assign a maximum two-day length of stay or less based on conventional length of stay guidelines, and perform daily concurrent review of additional days, requiring approval by an appropriate representative of HQM 13 as needed; and
(3) Assign a representative of HQM 13 to provide assistance to provider 16 in determining appropriate services to address the healthcare problem and to report treatments proposed by provider 16 to an appropriate representative of HQM 13.

All of the various intervention actions listed above are represented by steps 204 and 206 of FIG. 17. After all of the appropriate intervention actions have been completed, the healthcare request is fully processed. Additional healthcare requests may be received at step 194 and simultaneously processed.

By applying the resources of HQM 13 to intervene with those patients 14 presenting the greatest risk of generating high healthcare costs and providers 16 most likely to provide the least desirable healthcare, the method of the present invention may result in improvements to the healthcare consumption habits of patients 14 and to the practice patterns of providers 16, thereby resulting in an overall improvement of healthcare services consumed by patients 14 and cost efficiency realized by employer 10.

The foregoing description of the invention is illustrative only, and is not intended to limit the scope of the invention to the precise terms set forth. Although the invention has been described in detail with reference to certain illustrative embodiments, variations and modifications exist within the scope and spirit of the invention as described and defined in the following claims.

What is claimed is:

1. A method of optimizing healthcare services consumption of patients in one or more healthcare plans comprising:
    providing at least one computing device;
    the at least one computing device electronically receiving from a first external data source information comprising patient data,
    wherein the patient data comprises at least the names, ages, and genders of the patients in the one or more healthcare plans, wherein the patient data is for at least 9800 patients;
    the at least one computing device electronically receiving from a second external data source healthcare information comprising healthcare claims data relating to submitted medical claims and including at least a procedure code and costs;
    the at least one computing device analyzing, at least once during a predetermined time period, the healthcare claims data to determine a group of patients who are likely to consume healthcare services at a higher cost relative to other patients in the one or more healthcare plans;
    determining, based on the patient data and associated healthcare claims data, whether one or more patients in the group of patients suffers from one or more medical conditions,
    wherein determining whether one or more patients in the group of patients suffers from one or more medical conditions is repeated by the at least one computing device at least once during the predetermined time period;
    wherein each time one or more patients in the group of patients is determined to suffer from one or more medical conditions, the at least one computing device associates a predetermined set of minimum annual care requirements (MACRs) with the one or more patients' one or more medical conditions;
    the at least one computing device determining repeatedly during an annual period whether the one or more patients determined to suffer from one or more medical conditions has/have not obtained healthcare services that satisfy the predetermined set of MACRs associated with the one or more medical conditions; and
    transmitting, with an electronic communication device, an electronic message to an electronic device associated with a patient who has not obtained healthcare services that satisfy the predetermined set of MACRs to instruct the patient to obtain additional healthcare services to satisfy the predetermined set of MACRs from a healthcare service provider in a group of healthcare service providers who satisfy a quality based criterion.

2. The method of claim 1, wherein the at least one computing device stores the patient data each time a new patient is added to the one or more healthcare plans and stores the healthcare claims data each time a medical claim is submitted.

3. The method of claim 1, further comprising the at least one computing device receiving from a third external data source healthcare information comprising healthcare claims data relating to submitted pharmaceutical claims including at least a type and dosage of a prescribed drug.

4. The method of claim 1, wherein analyzing the healthcare claims data includes reviewing, by the at least one computing device, ages, genders, diagnoses, previously performed procedures and treatment of the patients in the one or more healthcare plans.

5. The method of claim 1, wherein the electronic message provides the electronic device associated with the patient with a list of providers from the group of healthcare service providers.

6. A method of optimizing healthcare services consumption of patients in one or more healthcare plans comprising:
    electronically receiving from a first external data source information comprising patient data including at least the names, ages and genders for at least 9800 patients;
    electronically receiving from a second external data source healthcare information comprising healthcare claims data relating to submitted medical claims;
    analyzing the healthcare claims data and the patient data to determine whether one or more patients suffers from one or more medical conditions;
    wherein each time one or more patients is determined to suffer from one or more medical conditions, associating a set of predetermined care requirements with the one or more patients' one or more medical conditions;
    determining, after a predetermined time period has passed since the one or more patients was determined to suffer from one or more medical conditions, whether healthcare claims data generated during the predetermined time period indicates that the one or more patients determined to suffer from one or more medical conditions has/have not obtained healthcare services that satisfy the set of predetermined care requirements associated with the one or more medical conditions; and
    transmitting an electronic message to an electronic device associated with a patient who has not obtained healthcare services that satisfy the set of predetermined care requirements to instruct the patient to obtain additional healthcare services to satisfy the set of predetermined care requirements from one or more providers in a group of healthcare service providers who satisfy a predefined quality based criteria.

7. The method of claim 6, wherein transmitting an electronic message includes transmitting a message to an electronic device associated with a healthcare service provider of the patient.

8. The method of claim 6, wherein transmitting an electronic message includes transmitting by at least one of a phone, an email system, or a fax machine.

9. The method of claim 6, further comprising transforming past practice patterns data of healthcare service providers into data representing the group of providers who satisfy the predefined quality-based criteria.

10. The method of claim 9, wherein transforming past practice patterns data includes rating providers who service patients in the one or more healthcare plans; wherein rating providers includes determining a cost efficiency index for each provider based on claim information by determining an average cost (AC1) for completed episodes of healthcare associated with the provider, determining an average cost (AC2) for similar episodes of health care treated by other providers who provide the same specialty service as the provider, dividing AC1 by AC2, and determining whether the cost efficiency index is less than a first predetermined threshold.

11. The method of claim 10, wherein rating providers further includes determining a service rating for each provider based on claim information by determining a number (N1) of preventative care services ordered by the provider for treatment of medical conditions, determining a number (N2) of preventative care services required to satisfy a predetermined set of preventative care services corresponding to the medical conditions, dividing N1 by N2, determining a typical service rate for other providers who provide the same specialty service as the provider, and determining whether the service rate for the provider is greater than a second predetermined threshold that represents a percentage of the typical service rate.

12. The method of claim 11, wherein rating providers further includes determining a practice patterns challenge rate for each provider based on claim information by determining a total number (T1) of undesirable practice characteristics associated with the provider, determining a typical number (T2) of undesirable practice characteristics associated with other providers who provide the same specialty service as the provider, dividing T1 by T2, and determining whether the practice patterns challenge rate is less than a third predetermined threshold.

13. The method of claim 12, wherein rating providers further includes associating an indication that a provider is in the group of healthcare service providers when the provider has a cost efficiency index that is less than the first predetermined threshold, a service rating that is greater than the second predetermined threshold, and a practice patterns challenge rate that is less than the third predetermined threshold.

14. A system for optimizing healthcare services consumption of patients in one or more healthcare plans comprising:
a first computing device including a database coupled with the first computing device, and one or more second computing devices electronically coupled with the first computing device via a network;
wherein the first computing device is configured to:
electronically receive from the one or more second computing devices and store in the database information comprising healthcare claims data and patient data for at least 9800 patients, the patient data including at least the names, ages and genders of the patients;
analyze, repeatedly during a predetermined time period, the healthcare claims data to determine a group of patients who are likely to consume healthcare services at a higher cost relative to other patients in the one or more healthcare plans;
determine, repeatedly during the predetermined time period, based on the patient data and the healthcare claims data, whether one or more patients in the group of patients suffer from one or more medical conditions;
determine repeatedly during an annual period whether the one or more patients determined to suffer from one or more medical conditions have not obtained healthcare services that satisfy a set of predetermined care requirements associated with the one or more medical conditions; and
an electronic communication device that is used to transmit an electronic message to an electronic device associated with a patient who has not obtained healthcare services that satisfy the set of predetermined care requirements to instruct the patient to obtain additional healthcare services to satisfy the set of predetermined care requirements from a determined group of healthcare service providers.

15. A method of optimizing healthcare services consumption, comprising:
assessing a healthcare situation of a population of patients that reside and consume healthcare services in a geographic zone consisting of a plurality of geographic regions, wherein assessing the healthcare situation includes
(i) accessing a database containing data relating to at least 9800 patients and providers who service the patients, the data including at least the names, ages and genders of the at least 9800 patients,
(ii) associating an address of each patient with a geographic region, and
(iii) associating a location of each provider with a geographic region;
transforming repeatedly during a predetermined time period past healthcare claims data generated by the patients into data representing a first group of patients likely to have higher consumption of healthcare services than other patients in the population;
transforming past practice patterns data generated by the providers in the geographic zone who provide services to the patients into data representing a first group of providers who satisfy at least one quality-based criterion;
contacting a patient before the patient consumes services to urge the patient to obtain the services from a provider in the first group of providers; and
determining during the predetermined time period whether patients in the first group of patients have obtained healthcare services that satisfy predetermined requirements, and, after a predetermined delay period, again determining during the predetermined time period whether patients in the first group of patients have obtained healthcare services that satisfy predetermined requirements.

16. The method of claim 15, wherein assessing a healthcare situation includes comparing costs associated with healthcare services in the geographic zone with costs of similar healthcare services in a geographic area that is larger than the geographic zone.

17. The method of claim 15, wherein transforming past healthcare claims data includes identifying patients suffering from at least one medical condition.

18. The method of claim 15, wherein transforming past healthcare claims data includes assigning a healthcare index to each patient based upon factors including age and gender of the patient.

19. The method of claim 15, wherein transforming past practice patterns data includes identifying episodes of healthcare for each of the providers in the geographic zone and comparing characteristics of the episodes of healthcare with characteristics of similar episodes of healthcare associated with providers in a geographic area that is larger than the geographic zone.

20. The method of claim 15, wherein transforming past practice patterns data includes performing an individual calculation for each provider in the geographic zone to determine the provider's cost efficiency index, and assigning a non-certified designation to each provider having cost efficiency index that fails to satisfy a first predetermined condition.

21. The method of claim 20, wherein transforming past practice patterns data includes performing an individual analysis for each provider to determine the provider's service rating, and assigning a non-certified designation to each provider having a service rating that fails to satisfy a second predetermined condition.

22. The method of claim 15, wherein transforming past practice patterns data further includes ranking other providers in the geographic zone not in the first group of providers based on an analysis of the quality and cost efficiency of practice patterns associated with the other providers, dividing the ranking of providers into a second group of other providers having a common characteristic and a third group of other providers having a common characteristic.

23. The method of claim 22, wherein ranking the other providers includes assigning a cost efficiency index to each of the other providers.

24. The method of claim 23, wherein ranking the other providers includes evaluating a practice pattern characteristic of each of the other providers.

25. The method of claim 22, wherein contacting a patient includes urging a patient who has obtained services from a third group provider to obtain future services from a second group provider.

26. The method of claim 25, further comprising conducting a first set of intervention actions if the patient uses a second group provider, the first set of intervention actions corresponding to a first degree of involvement of a healthcare quality management representative in the provision of services by the second group provider.

27. The method of claim 26, further comprising conducting a second set of intervention actions if the patient uses a third group provider, the second set of intervention actions corresponding to a second degree of involvement of the healthcare quality management representative in the provision of services by the third group provider, the second degree of involvement being greater than the first degree of involvement.

* * * * *